(12) United States Patent
Schaeffer et al.

(10) Patent No.: US 9,044,581 B2
(45) Date of Patent: Jun. 2, 2015

(54) MEDICAL DEVICES, METHODS, AND KITS FOR DELIVERING MEDICATION TO A BODILY PASSAGE

(71) Applicant: Cook Medical Technologies LLC, Bloomington, IN (US)

(72) Inventors: Darin Schaeffer, Bloomington, IN (US); Patrick Melder, Marietta, GA (US); Kathryn Evert, Bloomington, IN (US); Michael Boyd, Farmersville, OH (US); Dan Dalenberg, Bloomington, IN (US); Jack Kolenda, Mississauga (CA)

(73) Assignee: Cook Medical Technologies LLC, Bloomington, IN (US)

( * ) Notice: Subject to any disclaimer, the term of this patent is extended or adjusted under 35 U.S.C. 154(b) by 196 days.

(21) Appl. No.: 13/832,800

(22) Filed: Mar. 15, 2013

(65) Prior Publication Data
US 2013/0245609 A1    Sep. 19, 2013

Related U.S. Application Data

(60) Provisional application No. 61/612,604, filed on Mar. 19, 2012.

(51) Int. Cl.
*A61M 31/00* (2006.01)
*A61B 17/24* (2006.01)
(Continued)

(52) U.S. Cl.
CPC ............... *A61M 31/00* (2013.01); *A61B 17/24* (2013.01); *A61M 25/0113* (2013.01); *A61M 2210/0618* (2013.01); *A61M 25/0068* (2013.01); *A61M 25/007* (2013.01)

(58) Field of Classification Search
CPC ............ A61M 31/00; A61M 25/0113; A61M 2210/0618; A61M 25/0068; A61M 25/007; A61B 17/24
USPC .............. 604/59–61, 164.01, 164.07, 165.01, 604/218, 514, 516, 523, 528, 530–532; 606/108
See application file for complete search history.

(56) References Cited

U.S. PATENT DOCUMENTS

| | | | |
|---|---|---|---|
| 4,726,374 A | 2/1988 | Bales et al. | |
| 5,037,403 A | 8/1991 | Garcia | |

(Continued)

FOREIGN PATENT DOCUMENTS

| | | |
|---|---|---|
| EP | 2522386 | 11/2012 |
| WO | WO0170308 | 9/2001 |

(Continued)

OTHER PUBLICATIONS

ATOS Medical, Sinoject, screenshot of product information taken from Atos Medical company website (http://www.atosmedical.com/For_professionals/Focus_areas/~/media/Sweden/MC0766-NoEN.pdf) visited on Aug. 19, 2013.

(Continued)

*Primary Examiner* — Theodore Stigell
(74) *Attorney, Agent, or Firm* — Buchanan Nipper

(57) ABSTRACT

Medical devices, methods and kits are described. An exemplary medical device comprises a catheter that has a catheter wall and defines a catheter lumen, a bend, and a coil disposed distal to the bend. The catheter defines one or more apertures that extend through the catheter wall and are in communication with the catheter lumen.

20 Claims, 11 Drawing Sheets

(51) Int. Cl.
*A61M 25/01* (2006.01)
*A61M 25/00* (2006.01)

(56) References Cited

U.S. PATENT DOCUMENTS

| | | | |
|---|---|---|---|
| 5,180,362 A * | 1/1993 | Worst | 604/8 |
| 5,380,305 A | 1/1995 | Ghouri | |
| 5,460,616 A | 10/1995 | Weinstein et al. | |
| 5,522,400 A | 6/1996 | Williams | |
| 5,554,114 A | 9/1996 | Wallace et al. | |
| 5,603,694 A | 2/1997 | Brown et al. | |
| 5,624,396 A | 4/1997 | McNamara et al. | |
| 5,681,323 A * | 10/1997 | Arick | 606/108 |
| 5,685,858 A | 11/1997 | Kawand | |
| 5,738,664 A | 4/1998 | Erskine et al. | |
| 5,897,521 A | 4/1999 | Lavigne | |
| 5,908,403 A | 6/1999 | Bosma et al. | |
| 5,989,241 A | 11/1999 | Plishka et al. | |
| 6,159,177 A | 12/2000 | Amos, Jr. et al. | |
| 6,206,870 B1 | 3/2001 | Kanner | |
| 6,530,913 B1 | 3/2003 | Giba et al. | |
| 6,673,060 B1 | 1/2004 | Fleming, III | |
| 7,361,168 B2 | 4/2008 | Makower et al. | |
| 7,410,480 B2 | 8/2008 | Muni et al. | |
| 7,462,175 B2 | 12/2008 | Chang et al. | |
| 7,500,971 B2 | 3/2009 | Chang et al. | |
| 7,520,876 B2 | 4/2009 | Ressemann et al. | |
| 7,547,323 B2 | 6/2009 | Lavigne | |
| 7,559,925 B2 | 7/2009 | Goldfarb et al. | |
| 7,641,630 B2 | 1/2010 | Accisano, III et al. | |
| 7,645,272 B2 | 1/2010 | Chang et al. | |
| 7,654,997 B2 | 2/2010 | Makower et al. | |
| 7,678,099 B2 | 3/2010 | Ressemann et al. | |
| 7,717,933 B2 | 5/2010 | Becker | |
| 7,720,521 B2 | 5/2010 | Chang et al. | |
| 7,727,186 B2 | 6/2010 | Makower et al. | |
| 7,727,226 B2 | 6/2010 | Chang et al. | |
| 7,736,331 B2 | 6/2010 | Accisano, III et al. | |
| 7,740,608 B2 | 6/2010 | Lampropoulos et al. | |
| 7,740,642 B2 | 6/2010 | Becker | |
| 7,753,929 B2 | 7/2010 | Becker | |
| 7,753,930 B2 | 7/2010 | Becker | |
| 7,771,409 B2 | 8/2010 | Chang et al. | |
| 7,803,150 B2 | 9/2010 | Chang et al. | |
| 7,854,744 B2 | 12/2010 | Becker | |
| 7,879,061 B2 | 2/2011 | Keith et al. | |
| 7,909,814 B2 | 3/2011 | Accisano, III et al. | |
| 7,918,871 B2 | 4/2011 | Truitt et al. | |
| 7,959,644 B2 | 6/2011 | Shriver | |
| 8,083,879 B2 | 12/2011 | Swinehart et al. | |
| 8,088,101 B2 | 1/2012 | Chang et al. | |
| 8,090,433 B2 | 1/2012 | Makower et al. | |
| 8,100,933 B2 | 1/2012 | Becker | |
| 8,114,062 B2 | 2/2012 | Muni et al. | |
| 8,123,722 B2 | 2/2012 | Chang et al. | |
| 8,142,422 B2 | 3/2012 | Makower et al. | |
| 8,241,266 B2 | 8/2012 | Keith et al. | |
| 8,277,478 B2 | 10/2012 | Drontle et al. | |
| 8,277,503 B2 | 10/2012 | Lavigne | |
| 8,277,504 B2 | 10/2012 | Lavigne | |
| 8,282,667 B2 | 10/2012 | Drontle et al. | |
| 8,292,939 B2 * | 10/2012 | Yachia et al. | 623/1.11 |
| 8,317,816 B2 | 11/2012 | Becker | |
| 8,388,642 B2 | 3/2013 | Muni et al. | |
| 8,414,473 B2 | 4/2013 | Jenkins et al. | |
| 8,425,457 B2 | 4/2013 | John et al. | |
| 8,435,290 B2 | 5/2013 | Clifford et al. | |
| 8,496,645 B2 | 7/2013 | Eells et al. | |
| 8,603,185 B2 | 12/2013 | Shah et al. | |
| 8,657,805 B2 | 2/2014 | Peh et al. | |
| 8,734,426 B2 | 5/2014 | Ahmed et al. | |
| 2006/0004323 A1 | 1/2006 | Chang et al. | |
| 2007/0129751 A1 | 6/2007 | Muni et al. | |
| 2007/0167682 A1 | 7/2007 | Goldfarb et al. | |
| 2007/0208252 A1 | 9/2007 | Makower | |
| 2007/0208301 A1 | 9/2007 | Evard et al. | |
| 2007/0293727 A1 | 12/2007 | Goldfarb et al. | |
| 2008/0015472 A1 | 1/2008 | Ressemann et al. | |
| 2008/0015544 A1 | 1/2008 | Keith et al. | |
| 2008/0103521 A1 | 5/2008 | Makower et al. | |
| 2008/0119693 A1 | 5/2008 | Makower et al. | |
| 2008/0125756 A1 | 5/2008 | Dicarlo et al. | |
| 2008/0132938 A1 | 6/2008 | Chang et al. | |
| 2008/0172033 A1 | 7/2008 | Keith et al. | |
| 2008/0195041 A1 | 8/2008 | Goldfarb et al. | |
| 2008/0228085 A1 | 9/2008 | Jenkins et al. | |
| 2008/0275483 A1 | 11/2008 | Makower et al. | |
| 2008/0287908 A1 | 11/2008 | Muni et al. | |
| 2008/0319424 A1 | 12/2008 | Muni et al. | |
| 2009/0030274 A1 | 1/2009 | Goldfarb et al. | |
| 2009/0187098 A1 | 7/2009 | Makower et al. | |
| 2009/0198216 A1 | 8/2009 | Muni et al. | |
| 2009/0216196 A1 | 8/2009 | Drontle et al. | |
| 2009/0240112 A1 | 9/2009 | Goldfarb et al. | |
| 2009/0240237 A1 | 9/2009 | Goldfarb et al. | |
| 2009/0312745 A1 | 12/2009 | Goldfarb et al. | |
| 2010/0030113 A1 | 2/2010 | Morriss et al. | |
| 2010/0042046 A1 | 2/2010 | Chang et al. | |
| 2010/0076269 A1 | 3/2010 | Makower et al. | |
| 2010/0114066 A1 | 5/2010 | Makower et al. | |
| 2010/0152705 A1 | 6/2010 | Navis | |
| 2010/0168511 A1 | 7/2010 | Muni et al. | |
| 2010/0174138 A1 | 7/2010 | Chang et al. | |
| 2010/0174308 A1 | 7/2010 | Chang et al. | |
| 2010/0198191 A1 | 8/2010 | Clifford et al. | |
| 2010/0198247 A1 | 8/2010 | Chang et al. | |
| 2010/0211007 A1 | 8/2010 | Lesch, Jr. et al. | |
| 2010/0268245 A1 | 10/2010 | Chang et al. | |
| 2010/0274188 A1 | 10/2010 | Chang et al. | |
| 2010/0298862 A1 | 11/2010 | Chang et al. | |
| 2011/0004057 A1 | 1/2011 | Goldfarb et al. | |
| 2011/0040269 A1 | 2/2011 | Cline | |
| 2011/0060214 A1 | 3/2011 | Makower | |
| 2011/0071349 A1 | 3/2011 | Drontle et al. | |
| 2011/0112512 A1 | 5/2011 | Muni et al. | |
| 2011/0160740 A1 | 6/2011 | Makower et al. | |
| 2011/0224652 A1 | 9/2011 | Drontle et al. | |
| 2011/0288477 A1 | 11/2011 | Ressemann et al. | |
| 2012/0010646 A1 | 1/2012 | Keith et al. | |
| 2012/0071824 A1 | 3/2012 | Chang et al. | |
| 2012/0116254 A1 | 5/2012 | Morriss | |
| 2012/0136207 A1 | 5/2012 | Goldfarb et al. | |
| 2012/0172912 A1 | 7/2012 | Ressemann et al. | |
| 2012/0184983 A1 | 7/2012 | Chang et al. | |
| 2012/0190973 A1 | 7/2012 | Ressemann et al. | |
| 2012/0245419 A1 | 9/2012 | Makower et al. | |
| 2012/0265094 A1 | 10/2012 | Goldfarb et al. | |
| 2012/0283625 A1 | 11/2012 | Keith et al. | |
| 2013/0096605 A1 | 4/2013 | Becker | |
| 2013/0103004 A1 | 4/2013 | Gray et al. | |

FOREIGN PATENT DOCUMENTS

| | | |
|---|---|---|
| WO | WO2006020180 | 2/2006 |
| WO | WO2008045242 | 4/2008 |
| WO | WO2011082074 | 7/2011 |
| WO | WO2011084655 | 7/2011 |

OTHER PUBLICATIONS

Written Opinion of the International Searching Authority for International Application No. PCT/US2013/032125, Jul. 11, 2013, p. 1-7.
International Search Report for International Application No. PCT/US2013/032125, Jul. 11, 2013, p. 1-6.
The International Bureau of WIPO, International Preliminary Report on Patentability, Sep. 23, 2014, for International Application No. PCT/US2013/032125.
The American Laryngological, Rhinological and Otological Society, Inc., Francois Lavigne, MD et al., Intrasinus Administration of Topical Budesonide to Allergic Patients With Chronic Rhinosinusitis Following Surgery, May 2002, The Laryngoscope.

(56) References Cited

OTHER PUBLICATIONS

XprESS Multi-Sinus Dilation Tool. Instructions for Use, Entellus Medical, May 2011, pp. 1-7.

XprESS Multi-Sinus Dilation Tool Using Bending Tool. Instructions for Use, Entellus Medical, Sep. 2011, pp. 1-7.

* cited by examiner

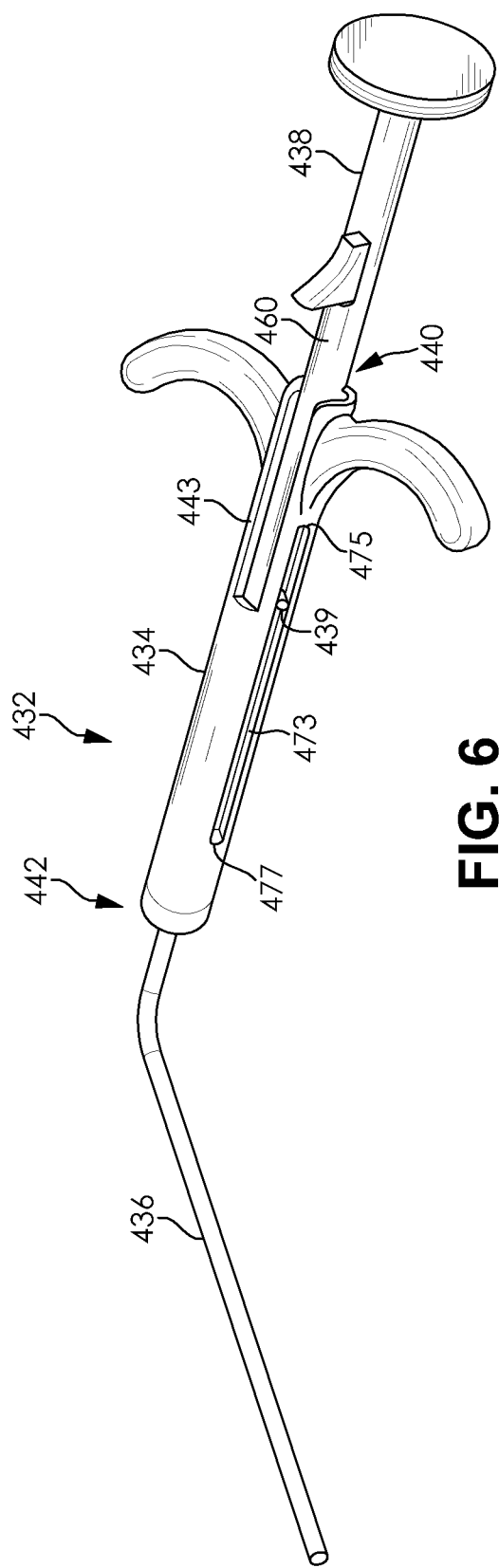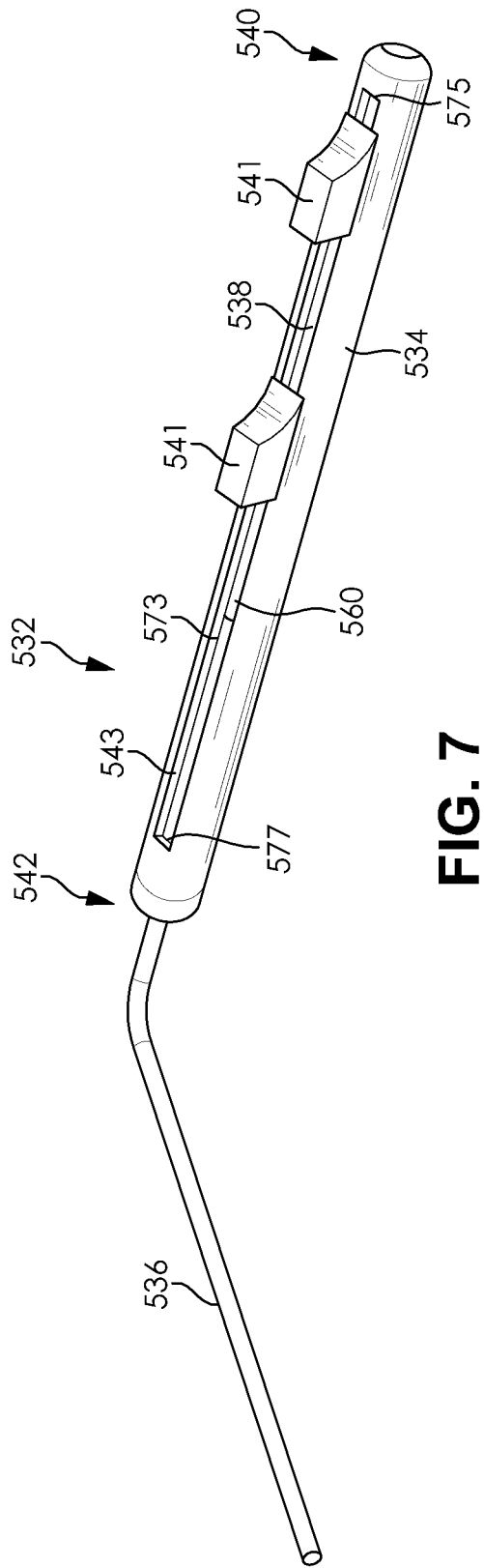

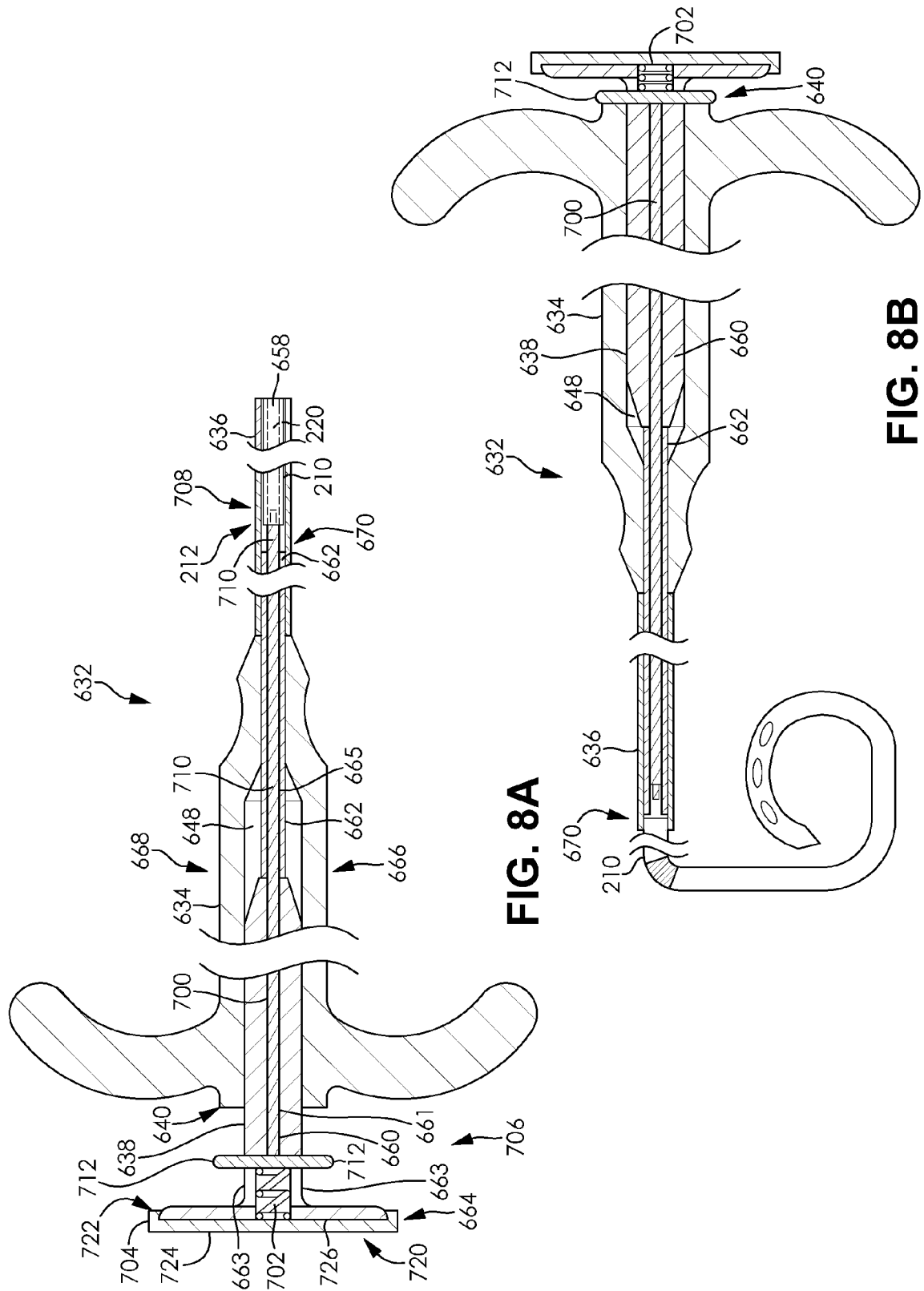

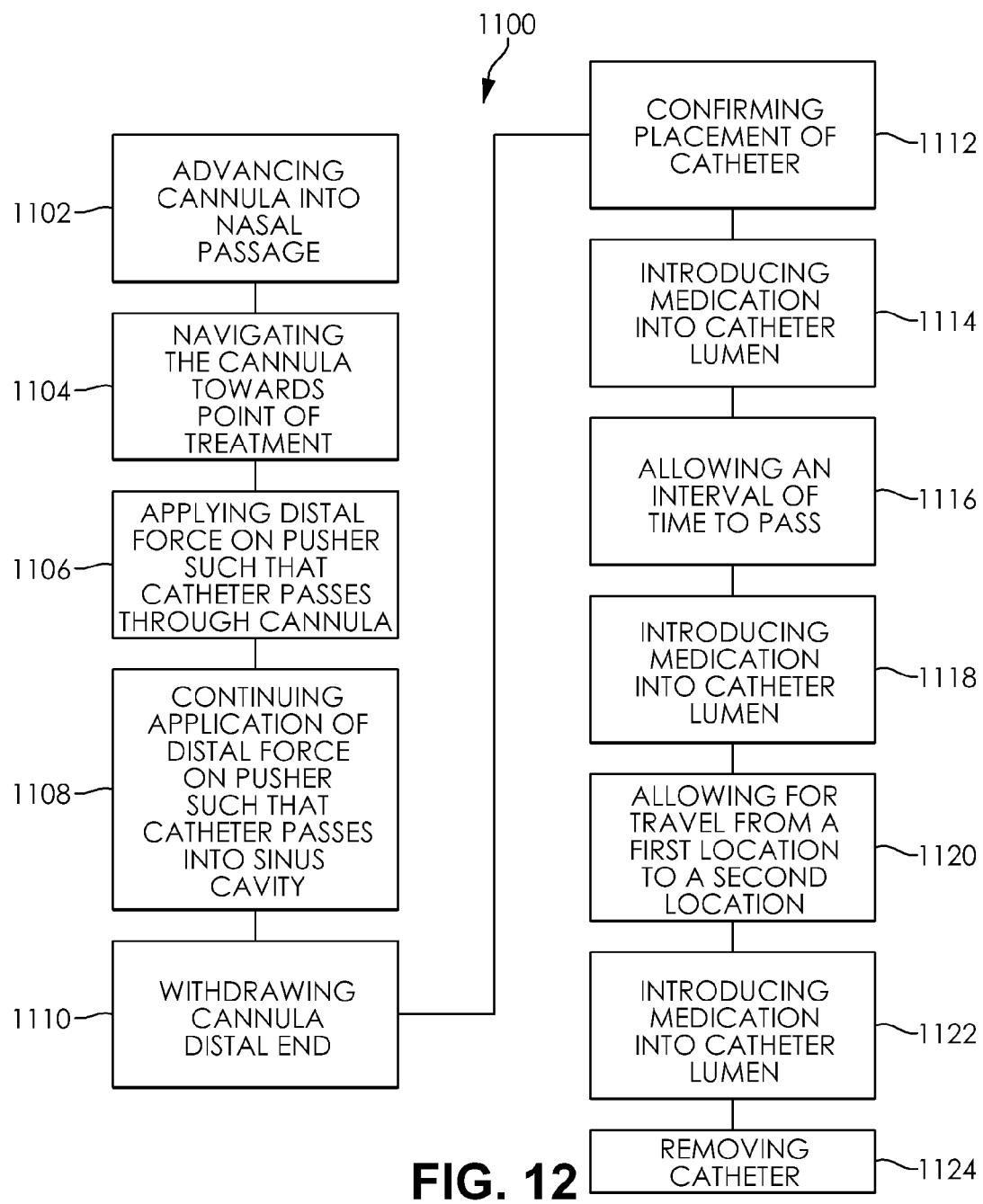
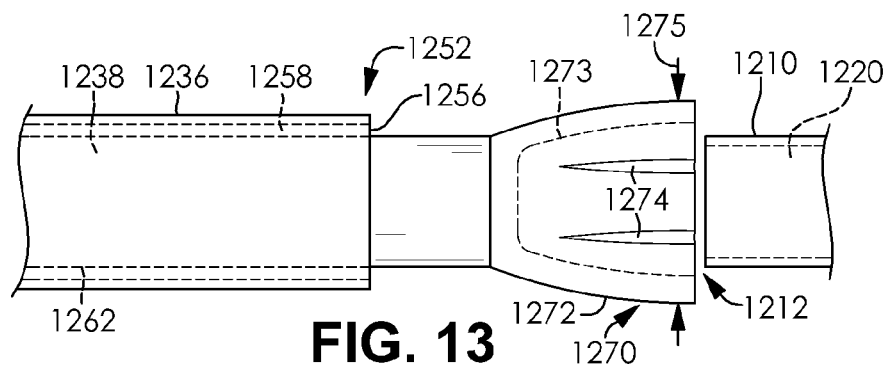
FIG. 12
FIG. 13

MEDICAL DEVICES, METHODS, AND KITS FOR DELIVERING MEDICATION TO A BODILY PASSAGE

RELATED APPLICATIONS

This application claims the benefit of U.S. Provisional Application No. 61/612,604, filed Mar. 19, 2012. The entire contents of this related application is hereby incorporated into this disclosure by reference.

FIELD

The disclosure relates generally to medical devices. More particularly, the disclosure relates to catheters useful in delivering a medication to a bodily passage, such as a sinus cavity. The disclosure also relates to delivery systems, methods and kits.

BACKGROUND

It is sometimes necessary or otherwise desirable to deliver a medication to a bodily passage, such as a sinus cavity. For example, when sinus cavities become infected or inflamed, delivering a medication to the affected area provides an approach to address the infection or inflammation. Conventional procedures include performing nasal rinses and using nebulizers to deliver a medication, such as therapeutic agents, into the nasal passages with hopes that some therapeutic agent will reach the infected or inflamed sinus cavity. These approaches, however, are minimally effective at delivering the medication to the sinus cavity because they rely on indirect delivery of the medication to the cavity.

While some methods of treatment achieve direct delivery of the medication to the cavity, these methods also have disadvantages. For example, a tube with an anchoring member at its distal end can be placed into the cavity to provide access for delivery. These devices and techniques, however, lack sufficient structure to achieve a uniform distribution of the medication throughout the cavity and placement of the tube must be done without the aid of a delivery system, which increases the complexity and time required to position the tube in the cavity. Also, the anchoring member occludes the sinus opening through which the tube has been deployed, which can block the natural outflow of material from the cavity.

A further alternative method of treatment involves the systemic administration of oral antibiotics and/or steroids. This approach, however, can have limited effectiveness and may lead to systemic consequences. For example, long-term use of corticosteroids has been associated with spasms of the large airways, fungus infection, decreased bone thickness, and/or growth impediments.

Therefore, a need exists for improved medical devices, methods and kits for delivering a medication to a bodily passage, such as a sinus cavity.

SUMMARY

Various exemplary medical devices, catheters, delivery systems, and methods are described.

An exemplary medical device for treating a sinus cavity comprises a delivery system and a catheter. The delivery system comprises a housing, a cannula, and a pusher. The housing has a housing proximal end, a housing distal end, and defines a first housing opening, a second housing opening, and a housing lumen. The housing lumen extends between the first housing opening and the second housing opening. The cannula has a cannula proximal end, a cannula distal end, and defines a first cannula opening, a second cannula opening, and a cannula lumen. The cannula lumen extends between the first cannula opening and the second cannula opening. The cannula is attached to the housing such that the housing lumen and the cannula lumen are in communication. The pusher has a pusher proximal end and a pusher distal end that is slidably disposed in the cannula lumen. The catheter has at least a portion disposed in the cannula lumen and has a catheter proximal end, a catheter distal end, and a catheter length that extends between the catheter proximal end and the catheter distal end. The catheter defines a first catheter opening, a second catheter opening, a bend, a coil, and a catheter lumen that extends between the first catheter opening and the second catheter opening. The pusher distal end is adapted to engage with the catheter proximal end to transfer axial movement to the catheter. The catheter is adapted to move between a first configuration in which the portion of the catheter that is disposed within the cannula lumen is substantially straight when disposed in the cannula lumen and a second configuration in which the catheter defines the bend and the coil along the catheter length when the catheter is free of the cannula lumen.

Another exemplary medical device for treating a sinus cavity comprises a delivery system and a catheter. The delivery system comprises a housing, a cannula, and a pusher. The housing has a housing proximal end, a housing distal end, and defines a first housing opening, a second housing opening, and a housing lumen. The housing lumen extends between the first housing opening and the second housing opening. The cannula has a cannula proximal end, a cannula distal end, and defines a first cannula opening, a second cannula opening, and a cannula lumen. The cannula lumen extends between the first cannula opening and the second cannula opening. The cannula is attached to the housing such that the housing lumen and the cannula lumen are in communication. The pusher has a pusher proximal end and a pusher distal end that is slidably disposed in the cannula lumen. The catheter has at least a portion disposed in the cannula lumen and has a catheter wall, a catheter proximal end, a catheter distal end, and a catheter length that extends between the catheter proximal end and the catheter distal end. The catheter defines a first catheter opening, second catheter opening, a plurality of apertures, a bend, a coil, and a catheter lumen. The first catheter opening is disposed on the catheter proximal end. The plurality of apertures is disposed along the catheter length and each aperture of the plurality of apertures extends through the catheter wall and is in communication with the catheter lumen. The coil and the plurality of apertures is disposed distal to the bend and the catheter lumen extends between the first catheter opening and the plurality of apertures. The pusher distal end is adapted to engage with the catheter proximal end to transfer axial movement to the catheter. The catheter is adapted to move between a first configuration in which the portion of the catheter that is disposed within the cannula lumen is substantially straight when disposed in the cannula lumen and a second configuration in which the catheter defines the bend and the coil along the catheter length when the catheter is free of the cannula lumen.

An exemplary method of deploying a medical device into a sinus cavity comprises the following steps: advancing a delivery system into a nasal passage such that a portion of the delivery system is disposed within the nasal passage, the delivery system comprising a housing, cannula, pusher, and a catheter; navigating the cannula toward a point of treatment; applying a distal force on the pusher such that the catheter is advanced into said sinus cavity and the catheter moves from the first substantially straight configuration to the second configuration; introducing medication into the catheter lumen and said sinus cavity; and withdrawing the delivery device from the nasal passage.

Kits useful in the performance of methods of treatment are also described.

An exemplary kit comprises a catheter and delivery system according to an embodiment. Kits can optionally include more than one catheter and/or delivery system according to an embodiment; one or more vials of medication, tools for introducing medication into a sinus cavity, instructions for use, and/or adaptors.

Additional understanding of the exemplary medical devices can be obtained by review of the detailed description, below, and the appended drawings.

BRIEF DESCRIPTION OF THE FIGURES

FIG. 6 illustrates a side view of another exemplary delivery system.
FIG. 7 illustrates a side view of another exemplary delivery system.
FIG. 8A illustrates a sectional view of another exemplary delivery system and catheter.
FIG. 8B illustrates a sectional view of the exemplary delivery system and catheter illustrated in FIG. 8A in a deployed configuration.
FIG. 12 is a flowchart representation of another exemplary method of treatment.
FIG. 13 illustrates a side view of the distal end of another exemplary delivery system and catheter.

DETAILED DESCRIPTION

The following detailed description and the appended drawings describe and illustrate various exemplary medical devices, kits and methods. The description and drawings are exemplary in nature and are provided to enable one skilled in the art to make and use one or more exemplary medical devices, kits, and/or practice one or more exemplary methods. They are not intended to limit the scope of the claims in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. As used herein, the terms "proximal" and "distal" are used to describe opposing axial ends of the particular elements or features being described. The use of "bodily passage" or "body passage" refers to any passage within the body of an animal, including, but not limited to, humans, and includes elongate passages. The term "sinus passage" refers to the nasal passages and includes, but is not limited to, eustachian tube(s), primary ostium, accessory ostium, and/or an opening defined by a ventilation tube. The term "sinus cavity" refers to the frontal, ethmoid, sphenoid, and/or maxillary sinus. The term "medication" refers to any fluid, drug, agent, and/or therapeutic agent used to treat a patient. The use of "exemplary" refers to "an example of" and is not intended to convey a meaning of an ideal or preferred embodiment. The use of "attached" refers to the fixed, releasable, or integrated association of two or more elements and/or devices. Thus, the term "attached" includes releasably attaching or fixedly attaching two or more elements and/or devices. The term "coil" refers to a length of an element that is arranged in one or more complete or partial spirals, loops, and/or rings. The term "coil" does not require regularity in the arrangement of the one or more spirals, loops, and/or rings and does not require that an entire spiral, loop, and/or ring be formed.

Figure 1:
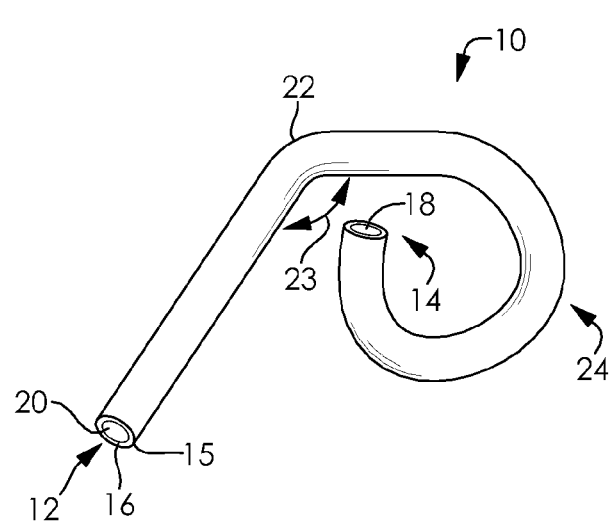
FIG. 1 illustrates a side view of an exemplary catheter.

FIG. 1 illustrates a first exemplary catheter 10 having a catheter proximal end 12, a catheter distal end 14, and a catheter wall 15. Catheter 10 defines a first catheter opening 16, a second catheter opening 18, a lumen 20, a bend 22, a coil 24, and a catheter length that extends from the catheter proximal end 12 to the catheter distal end 14. Catheter 10 is adapted to move between a first configuration in which the catheter is substantially straight (e.g., when the catheter is disposed within a delivery system) and a second configuration in which the catheter defines bend 22 and coil 24 (e.g., when the catheter is free of the delivery system). FIG. 1 illustrates catheter 10 in the second configuration.

Catheter 10 can comprise any suitable tubular member having any suitable outside diameter and any suitable inside diameter defining a lumen, and skilled artisans will be able to select a suitable tubular member according to a particular embodiment based on various considerations, including the desired bodily passage within which the catheter is intended to be used. The inventors have determined that catheters having an outside diameter between about 0.05 inches to about 0.1 inches are suitable. In addition, the inventors have determined that catheters having an outside diameter about, equal to, or substantially equal to 0.077 inches are also suitable. Furthermore, the inventors have determined that catheters having an inside diameter between about 0.025 inches to about 0.075 inches are suitable. Moreover, the inventors have determined that catheters having an inside diameter about, equal to, or substantially equal to 0.050 inches are also suitable.

Catheter 10 can be formed of any suitable flexible, or substantially flexible, material, and skilled artisans will be able to select a suitable material for a catheter according to a particular embodiment based on various considerations, including the bodily passage within which the catheter is intended to be used. The material selected for a catheter need only be biocompatible, or able to be made biocompatible, and able to move between a first configuration and a second configuration, as described herein. Also, it is considered advantageous to select a material for a catheter that is relatively soft and/or supple at least because such a material allows for the catheter to be passed through tortuous bodily passages and reduces irritation when the catheter is disposed in a bodily passage. Example materials considered suitable include, but are not limited to, polymers, such as urethane, polyurethane, polyethylene, Pebax (Pebax is a registered trademark of Ato Chimie Corporation of Allee des Vosges, Courbevoie, France), silicone, and nylon.

Catheter 10 can optionally include a radiopaque marker disposed at catheter proximal end 12, catheter distal end 14, and/or along any portion, or the entirety, of the catheter length (e.g., at bend 22, at coil 24), to facilitate tracking and positioning of catheter 10 during, or subsequent to, deployment. Alternative, or in combination, with providing a radiopaque marker disposed on catheter 10, the material forming catheter 10 can include a radiopaque filler to facilitate tracking and positioning of catheter 10. Any suitable radiopaque material can be used, and skilled artisans will be able to select a suitable radiopaque material according to a particular embodiment based on various considerations, such as the desired bodily passage within which a catheter is intended to be deployed. Examples of suitable radiopaque materials include, but are not limited to, cadmium, tungsten, gold, tantalum, bismuth, platinum, iridium, and rhodium. Visualization, tracking, and/or positioning of catheter 10 can be accomplished using any suitable method, and skilled artisans will be able to select a suitable method according to a particular embodiment based on various considerations, such as the desired bodily passage within which a catheter is intended to be deployed. Example methods considered suitable to facilitate visualization, tracking, and/or positioning of a catheter include, but are not limited to, using x-ray, fluoroscopy, ultrasound, direct visualization with a scope, and magnetic resonance imaging.

The first catheter opening 16 is defined on the catheter proximal end 12 and the second catheter opening 18 is defined on the catheter distal end 14. Each of the first catheter opening 16 and the second catheter opening 18 are in communication with lumen 20 and can have any suitable diameter. While the first catheter opening 16 and the second catheter opening 18 have been described and illustrated as defined on the catheter proximal end 12 and the catheter distal end 14, respectively, a first catheter opening and a second catheter opening can be positioned at any suitable location along the catheter length. Skilled artisans will be able to select a suitable position for each of a first catheter opening and a second catheter opening according to a particular embodiment based on various considerations, including the desired bodily passage within which the catheter is intended to be used. For example, either, or both of a first catheter opening and a second catheter opening can be defined along the length of a catheter between the catheter proximal end and the catheter distal end and extend through the wall of a catheter.

Lumen 20 extends between the first catheter opening 16 and the second catheter opening 18. Lumen 20 can have any suitable inner diameter along the catheter length, and skilled artisans will be able to select a suitable inner diameter according to a particular embodiment based on various considerations, including the desired bodily passage within which the catheter is intended to be used. Example inner diameters considered suitable include, but are not limited to, inner diameters that are continuous, or substantially continuous, along the catheter length, and inner diameters that vary along the catheter length.

When in the second configuration, catheter 10 defines bend 22 and coil 24 along the catheter length. In the illustrated embodiment, bend 22 defines an angle 23 greater than 90 degrees between the portion of the catheter 10 proximal to bend 22 and the portion of the catheter distal to bend 22. A length of catheter 10 is disposed distal to bend 22 that defines a distance between the portion of the catheter distal to bend 22 (e.g., coil 24) and the portion of the catheter 10 proximal to bend 22 when the catheter 10 is in the second configuration. This is considered advantageous at least because it allows the catheter 10 to be positioned such that coil 24 is disposed within a first bodily passage (e.g., a sinus cavity) and the portion of the catheter proximal to bend 22 is disposed within a second, different, bodily passage (e.g., a nasal passage).

While catheter 10 has been described and illustrated as defining a bend 22 at a particular angle, any suitable angle can be defined by a catheter, and skilled artisans will be able to select a suitable angle for a bend according to a particular embodiment based on various considerations, including the desired bodily passage within which the catheter is intended to be used. The inventors have determined that angles between about 1 degree to about 180 degrees are suitable. Also, the inventors have determined that angles between about 10 degrees and about 170 degrees are suitable. In addition, the inventors have determined that angles between about 45 degrees and about 135 degrees are suitable. Furthermore, the inventors have determined that an angle of about, equal to, or substantially equal to 90 degrees is also suitable. Moreover, the inventors have determined that an angle of about, equal to, or substantially equal to 150 degrees is also suitable.

In addition, while catheter 10 has been described and illustrated as defining a distance between the portion of the catheter distal to bend 22 (e.g., coil 24) and the portion of the catheter 10 proximal to bend 22 when the catheter 10 is in the second configuration, other structural arrangements are considered suitable. Skilled artisans will be able to select a suitable structural arrangement for a catheter according to a particular embodiment based on various considerations, including the desired bodily passage within which a catheter is intended to be deployed. For example, alternative to defining a distance between a portion of the catheter distal to bend and a portion of the catheter proximal to bend when the catheter is in the second configuration, the catheter can omit the inclusion of a length of catheter distal to the bend such that the portion of the catheter distal to the bend (e.g., coil 24) overlaps, or extends over, the portion of the catheter proximal to the bend.

Catheter 10 defines coil 24 distal to bend 22. Coil 24 advantageously provides a structure for maintaining the position of the catheter 10 within a bodily passage upon deployment, as described in more detail herein. When the catheter 10 is in the second configuration, coil 24 is free of the portion of catheter 10 disposed proximal to bend 22 such that it does not wrap around the portion of catheter 10 disposed proximal to bend 22.

Alternatively, or in combination with the other structural details described herein (e.g., bend, coil), a catheter can include additional structure that is capable, or adapted to, maintain the catheter within a bodily passage. Example structures considered suitable to include on a catheter include, but are not limited to, malecot structures, cuffs, one or more balloons, and any other structure considered suitable for a particular application. The additional structure can be positioned on the catheter at any suitable location, proximal to a bend, distal to a bend, at a bend, at a coil, in place of a coil, in place of a bend, between the proximal and distal end, and any other location considered suitable for a particular application. For example, if a balloon is used to maintain the position of a catheter within a bodily passage, the catheter can define a second lumen that is in communication with a chamber defined by the balloon such that fluid can be introduced into the balloon chamber to inflate the balloon.

Coil 24 can comprise any suitable length, define any suitable outside diameter, define any suitable number of coils, and extend in any suitable arrangement, and skilled artisans will be able to select a suitable length, outside diameter, number of coils, and arrangement for a coil according to a particular embodiment based on various considerations, including the desired bodily passage within which the catheter is intended to be used. The inventors have determined that catheters defining a coil having an outside diameter between about 0.35 inches to about 0.85 inches are suitable. In addition, the inventors have determined that catheters defining a coil having an outside diameter about, equal to, or substantially equal to 0.59 inches are also suitable. It is considered advantageous for a catheter to define a single coil at least because this increases the manufacturability of the catheter. In addition, a catheter that defines multiple coils requires a greater catheter length and a longer delivery system than a catheter that defines a single coil.

In use, catheter 10 provides a mechanism for introducing a medication, or other material or fluid, into a bodily passage (e.g., sinus cavity). For example, subsequent to deployment, a syringe, or other structure, can be attached to the catheter proximal end 12 and used to introduce a medication or fluid through first catheter opening 16, the catheter lumen 20, and the second catheter opening 18.

Catheter 10 can be formed using any suitable technique to achieve a desired structural arrangement (e.g., bend 22, coil 24), and skilled artisans will be able to select a suitable technique to form a catheter according to a particular embodiment based on various considerations, including the bodily passage within which the device is intended to be used. An example technique considered suitable to form a catheter includes, but is not limited to, using heat to import memory into the catheter. For example, a forming plate can be used to force the catheter into a desired shape. This can be accomplished by placing a material into the catheter lumen to prevent its collapse during formation, placing the catheter in the forming plate, and then heating the catheter to a suitable temperature. Subsequently, the catheter is cooled to room temperature and removed from the forming plate. Any suitable temperature can be used to form a catheter, and skilled artisans will be able to select a suitable temperature according to a particular embodiment based on various considerations, such as the material that forms the catheter. For example, the inventors have determined that when a catheter is formed of urethane, suitable temperatures to achieve a desired structural arrangement include temperatures between about 108 degrees Celsius to about 158 degrees Celsius. In addition, the inventors have determined that when a catheter is formed of urethane, a suitable temperature to achieve a desired structural arrangement includes a temperature about, equal to, or substantially equal to 133 degrees Celsius.

Figure 2:
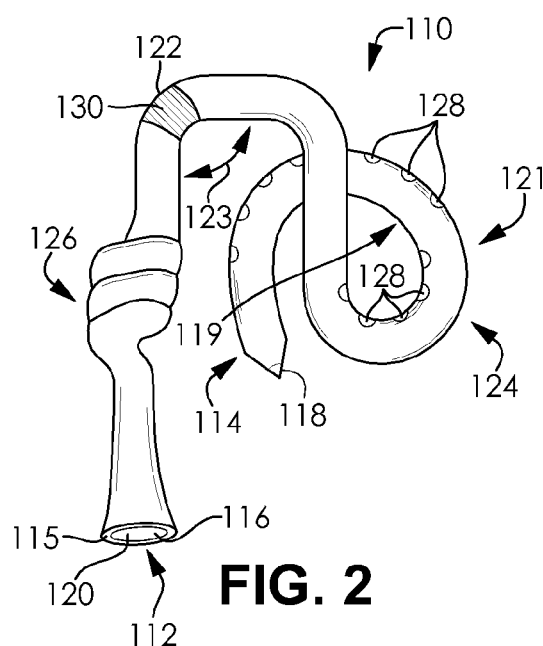
FIG. 2 illustrates a side view of another exemplary catheter.

FIG. 2 illustrates a second exemplary catheter 110. The catheter 110 is similar to catheter 10 illustrated in FIG. 1, and described above, except as detailed below. Reference numbers in FIG. 2 refer to the same structural element or feature referenced by the same number in FIG. 1, offset by 100. Thus, catheter 110 has a catheter proximal end 112, a catheter distal end 114, and defines a first catheter opening 116, a second catheter opening 118, and a lumen 120.

In the illustrated embodiment, catheter 110 defines a flared catheter proximal end 112 and flared lumen 120 at the catheter proximal end 112, a tapered catheter distal end 114, a bend 122, a first coil 124, a second coil 126, and a plurality of apertures 128. In addition, catheter 110 includes a marker 130 disposed at bend 122. Catheter 110 is adapted to move between a first configuration in which the catheter 110 is substantially straight (e.g., when the catheter is disposed within a delivery system) and a second configuration in which the catheter 110 defines bend 122, first coil 124, and second coil 126 (e.g., when the catheter is free of the delivery system). FIG. 2 illustrates catheter 110 in the second configuration.

Including a flared catheter proximal end 112 and flared lumen 120 at the catheter proximal end 112 is considered advantageous at least because it provides a structural arrangement that allows for the introduction of another device (e.g., syringe, adaptor) into the first catheter opening 116 to pass a medication or fluid through lumen 120 and the plurality of apertures 128. Including a tapered catheter distal end 114 is considered advantageous at least because it provides a structural arrangement that allows for the dilation of an opening of a bodily passage during deployment of the catheter 110, ease of insertion atraumatically, and/or reduces the likelihood of the catheter distal end 114 from catching on a structure. For example, when the catheter 110 is advanced over a previously placed wire guide and into a bodily passage, providing a tapered catheter distal end 114 provides a mechanism for dilating the bodily passage and advancing past structures during deployment. Optionally, in instances where a catheter has been formed of a soft material (e.g., urethane), a stiffer material can be bonded to the softer material along a portion, or the entirety, of the catheter length to assist with dilation and positioning of the catheter within a bodily passage.

In the illustrated embodiment, catheter 110 defines bend 122 at an angle 123 equal to, substantially equal to, or about 90 degrees. It is considered advantageous for catheter 110 to define bend 122 at an angle equal to, substantially equal to, or about 90 degrees at least to provide a structural arrangement that allows catheter 110 to be held in place upon deployment. For example, when a portion, or the entirety, of catheter 110 is deployed in a sinus passage and/or sinus cavity, defining bend 122 at an angle equal to, substantially equal to, or about 90 degrees allows for a portion, or the entirety, of the catheter proximal to bend 122 to extend through the sinus passage and out of the nostril and a portion, or the entirety, of the catheter distal to bend 122 to be disposed within the sinus passage and/or sinus cavity, while preventing obstruction of the sinus passage and irritation.

While bend 122 has been illustrated as defining a curve along the length of catheter 110, a bend can define any suitable structure and/or feature along the length of a catheter, and skilled artisans will be able to select a suitable structure and/or feature to include in a catheter according to a particular embodiment based on various considerations, including the desired bodily passage within which the catheter is to be deployed. Example structures and/or features considered suitable to include on a catheter include, but are not limited to, defining a corner at a right angle at a bend in the catheter, defining a curve at a right angle at a bend in the catheter, defining a corner at any suitable angle at a bend in the catheter, defining a curve at any suitable angle at a bend in the catheter, defining a hard corner at a right angle at a bend in the catheter such that at least one point is defined along the catheter length at the corner, and defining a hard corner at any suitable angle at a bend in the catheter such that at least one point is defined along the catheter length at the corner.

Catheter 110 defines the first coil 124 distal to bend 122. First coil 124 advantageously provides a structural arrangement for maintaining the position of the catheter 110 within a bodily passage upon deployment, as described herein. When the catheter 110 is in the second configuration, first coil 124 is free of the portion of catheter 110 disposed proximal to bend 122 such that it does not wrap around the portion of catheter 110 disposed proximal to bend 122.

The plurality of apertures 128 is disposed distal to bend 122, extend through the wall 115 of the catheter 110 and each aperture of the plurality of apertures 128 is in communication with the catheter lumen 120. In the illustrated embodiment, the a first set and a second set of the plurality of apertures 128 are disposed linearly on first coil 124. This arrangement is considered advantageous at least because it positions the plurality of apertures 128 along the first coil 124 such that a first set of apertures from the plurality of apertures 128 is disposed on an outwardly facing side 121 of the first coil 124 and a second set of apertures from the plurality of apertures 128 is disposed on an inwardly facing side 119 of the first coil 124.

While the plurality of apertures 128 has been described and illustrated as arranged linearly along the first coil 124, any suitable arrangement of a plurality of apertures is considered suitable, and skilled artisans will be able to select a suitable arrangement for a plurality of apertures according to a particular embodiment based on various considerations, including the desired amount of medication or fluid to be delivered to a bodily passage, such as a sinus cavity. Example arrangements considered suitable to arrange a plurality of apertures, or a set thereof, along a portion, or the entirety, of a catheter and/or coil include, but are not limited to, arranging the apertures circumferentially, linearly, spirally, randomly, regularly, in a grid, and/or staggered.

Also, while a plurality of apertures 128 has been described and illustrated, any suitable number of apertures can be included in a catheter and each aperture can define any suitable diameter and/or shape. Skilled artisans will be able to select a suitable number of apertures for a catheter and a suitable diameter and/or shape for each aperture according to a particular embodiment based on various considerations, including the treatment intended to be performed. Example numbers of apertures considered suitable include one, two, three, four, five, six, seven, eight, nine, ten and any number determined suitable for a particular application. Example diameters considered suitable include, but are not limited to, diameters where at least two of the plurality of apertures 128 vary in diameter (e.g., have different diameters). Further example diameters considered suitable include, but are not limited to, diameters which are about, equal to, less than, greater than, or substantially equal to the inside diameter of the tubular member (e.g., diameter of lumen). Example shapes considered suitable to define an aperture include, but are not limited to, circular, oval, oblong, and any suitable polygonal shape. For example, when delivery of a medication or fluid at a greater flow rate is desired, a catheter can define an aperture having an oval or oblong shape which is longer on its lengthwise axis than the inside diameter of the catheter.

Catheter 110 defines the second coil 126 proximal to bend 122. Second coil 124 is adapted to move between a first straight, or substantially straight, configuration and a second coiled configuration. FIG. 2 illustrates the second coil 126 in the second coiled configuration. The second coil 126 advantageously provides a structural arrangement for maintaining a length of catheter 110 proximal to bend 122 within a bodily passage when catheter 110 is in its second configuration. For example, when the first coil 124 has been deployed in a sinus cavity and the second coil 126 has been positioned in a nasal passage, a user can place a proximal force on the catheter proximal end 112 to move the second coil 126 from its second coiled configuration to its first straight, or substantially straight, configuration such that the catheter proximal end 112 extends out of the nostril. This advantageously allows for a user to extend the catheter 110 out of the nostril to pass a medication or fluid through the lumen 120 of the catheter 110, while allowing the second coil 126 to move back to its second coiled configuration and into the nasal passage upon the release of the proximal force on the catheter 110.

Marker 130 is disposed at bend 122, can extend around a portion, or the entirety, of catheter 110, and can have any suitable length along the catheter length. Marker 130 can be formed in any suitable manner. For example, marker 130 can be embedded within, or disposed on the inner diameter of catheter lumen 120, and/or on the exterior surface of catheter 110. It is considered advantageous to include marker 130 at least to assist a user in accurately placing the catheter 110 within a bodily passage. Also, marker 130 advantageously indicates the location of bend 122 during deployment of catheter 110 and provides an indication as to when coil 124 has been deployed. While a single marker 130 has been illustrated and described, a catheter can have any suitable number of markers, and skilled artisans will be able to select a suitable number of markers according to a particular embodiment based on various considerations, such as the desired bodily passage within which the catheter is intended to be deployed. Example numbers of markers considered suitable include, but are not limited to, one, two, three, four and any other number considered suitable for a particular application.

Alternative to, or in combination with, using a marker 130, a catheter can comprise a first portion having a first color (e.g., red) and a second portion having a second color (e.g., blue) that is different than the first color. The first portion having a first color and a second portion having a second color can be disposed at any suitable location along the length of a catheter. Example locations considered suitable include, but are not limited to, positioning a first portion having a first color along a portion, or the entirety, of the length of a catheter disposed proximal to a bend or coil and positioning a second portion having a second color along a portion, or the entirety, of the length of the catheter disposed distal to a bend or coil. Any suitable number of portions of a catheter can have any suitable color to assist with placement of a catheter within a bodily passage. A color can be disposed on a surface of the catheter (e.g., painted) or comprise part of the material forming a catheter.

Alternative to including a single marker, a catheter can include more than one marker or an elongated marker that extends along a portion, or the entirety, of the length of catheter disposed proximal to a bend or coil. For example, a first marker can be positioned at a bend or coil and a second marker can be positioned proximal to the first marker (e.g., on catheter proximal end, between catheter proximal end and a bend or coil) or an elongated marker can be positioned between a catheter proximal end and a bend or coil, or from a bend or coil to the catheter proximal end or a location between the bend or coil and the catheter proximal end. Inclusion of an elongated marker or more than one marker is considered advantageous at least because it provides a mechanism for indicating placement of the catheter relative to a particular portion of a bodily passage (e.g., frontal recess, marker can be disposed adjacent to the frontal recess and/or a coil can be positioned in a frontal sinus).

Figure 3:
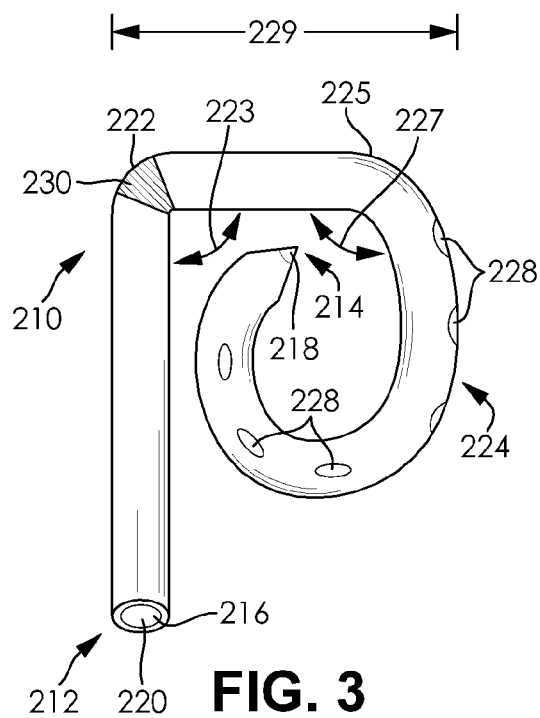
FIG. 3 illustrates a side view of another exemplary catheter.

FIG. 3 illustrates a third exemplary catheter 210. The catheter 210 is similar to catheter 110 illustrated in FIG. 2, and described above, except as detailed below. Reference numbers in FIG. 3 refer to the same structural element or feature referenced by the same number in FIG. 2, offset by 100. Thus, catheter 210 has a catheter proximal end 212, a catheter distal end 214, and defines a first catheter opening 216, a second catheter opening 218, and a lumen 220.

In the illustrated embodiment, catheter 210 defines a tapered catheter distal end 214, a first bend 222, a coil 224, a second bend 225, and a plurality of apertures 228. In addition, catheter 210 includes a marker 230 disposed at bend 222. Catheter 210 is adapted to move between a first configuration in which the catheter 210 is substantially straight (e.g., when the catheter is disposed within a delivery system) and a second configuration in which the catheter 210 defines first bend 222, coil 224, and second bend 225 (e.g., when the catheter is free of the delivery system). FIG. 3 illustrates catheter 210 in the second configuration.

Catheter 210 defines first bend 222 at a first angle 223 and defines second bend 225 at a second angle 227. A length of catheter 229 is disposed between the first bend 222 and the second bend 225. It is considered advantageous to include a second bend 225 to complement the natural anatomy of the bodily passage within which the catheter is intended to be deployed (e.g., sinus cavity). The length of catheter 229 disposed between the first bend 222 and second bend 225 can be any suitable length, and skilled artisans will be able to select a suitable length according to a particular embodiment based on various considerations, including the desired bodily passage within which a catheter is intended to be disposed.

In the illustrated embodiment, catheter 210 defines bend 222 at an angle 223 equal to, substantially equal to, or about 90 degrees and defines bend 225 at an angle 227 greater than 90 degrees. While catheter 210 has been described and illustrated as defining first bend 222 and second bend 225 at particular angles, a catheter can define a first bend and a second bend at any suitable angle, such as those described herein, and skilled artisans will be able to select a suitable angle for a first bend and/or a second bend according to a particular embodiment based on various considerations, including the desired bodily passage within which the catheter is intended to be used. Example angles considered suitable to form a first bend and a second bend include, but are not limited to, defining a first bend at an angle greater than, less than, equal to, or substantially equal to, the angle of a second bend.

In addition, while catheter 210 has been described and illustrated as defining a first bend 222 and a second bend 225, a catheter can define any suitable number of bends along the catheter length, and skilled artisans will be able to select a suitable number of bends according to a particular embodiment based on various considerations, including the desired bodily passage within which the catheter is intended to be used. Example number of bends considered suitable include, but are not limited to, one, two, three, four, five, and any other number considered suitable for a particular application. For example, catheter 210 can optionally omit the inclusion of second bend 225.

Any of the herein described catheters can be deployed in a bodily passage using any suitable method of delivery, and skilled artisans will be able to select a suitable method of delivery according to a particular embodiment based on various considerations, including the desired bodily passage within which the catheter is intended to be used. Example methods of deployment considered suitable, include, but are not limited to, delivering a catheter over a previously placed guide wire, delivering a catheter using a trocar, and delivering a catheter using a delivery system, such as one of the delivery systems described herein.

Any of the herein described catheters can optionally include one or more coatings disposed on a portion, or the entirety, of the catheter to prevent biofilm formation (e.g., on the catheter, within the bodily passage), prevent or reduce microbial colonization (e.g., on the catheter, within the bodily passage), and/or reduce the coefficient of friction between the outer surface of a catheter and the surface in which the outer surface of the catheter is intended to, or may, contact. Any suitable coating capable of preventing biofilm formation on a catheter and/or capable of reducing the coefficient of friction is considered suitable, and skilled artisans will be able to select a suitable coating according to a particular embodiment based on various considerations, such as the bodily passage within which the catheter is intended to be used. A coating can be included along any suitable portion, or the entirety, of the catheter length. Example coatings considered suitable include, but are not limited to, rifampin, minocycline, chitosan, antibiotics such as aminoglycosides, quinolones, tetracyclines, and beta-lactams, antifungals such as azoles, and/or antiseptics. Examples lubricious coatings considered suitable to reduce the coefficient of friction include, but are not limited to, hydrophilics, polymers such as polytetrafluoroethylene (PTFE), and any other polymer or substance having properties that result in the lowering of the coefficient of friction between the outer surface of a catheter and the surface in which the outer surface of the catheter is intended to, or may, contact.

Any of the elements, features, and/or structural arrangements described herein with respect to any catheter can be combined in any suitable manner, and skilled artisans will be able to select a suitable element, feature, and/or structural arrangement for a catheter according to a particular embodiment based on various considerations, such as the desired bodily passage within which the catheter is intended to be deployed.

Figure 3A:
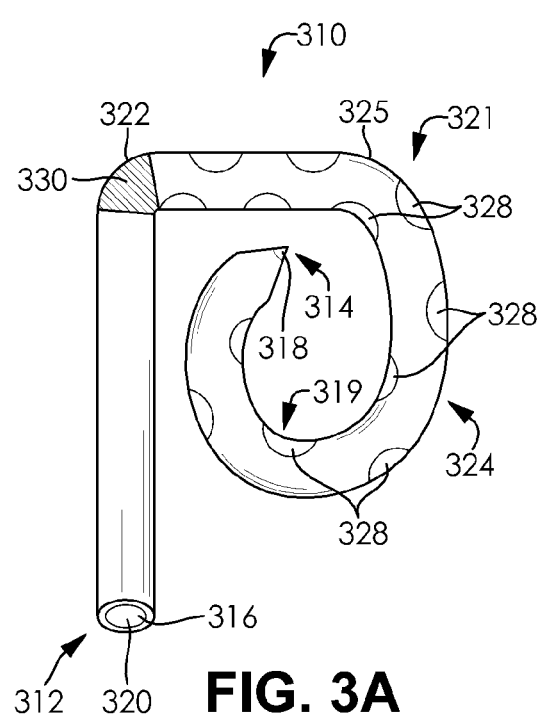
FIG. 3A illustrates a side view of another exemplary catheter.

For example, FIG. 3A illustrates a fourth exemplary catheter 310. The catheter 310 is similar to catheter 210 illustrated in FIG. 3, and described above, except as detailed below. Reference numbers in FIG. 3A refer to the same structural element or feature referenced by the same number in FIG. 3, offset by 100. Thus, catheter 310 has a catheter proximal end 312, a catheter distal end 314, and defines a first catheter opening 316, a second catheter opening 318, and a lumen 320.

In the illustrated embodiment, catheter 310 defines a plurality of apertures 328 such that a first set of apertures is disposed on an inwardly facing side 319 of coil 324 and a second set of apertures is disposed on an outwardly facing side 321 of coil 324. The first set of apertures disposed on the inwardly facing side 319 of coil 324 is staggered relative to the second set of apertures disposed on the outwardly facing side 321 of coil 324. This arrangement is considered advantageous at least because it positions the plurality of apertures 328 along the coil 324 such that delivery of a medication or fluid can be accomplished throughout the bodily passage within which the catheter 310 is disposed.

Figure 4:
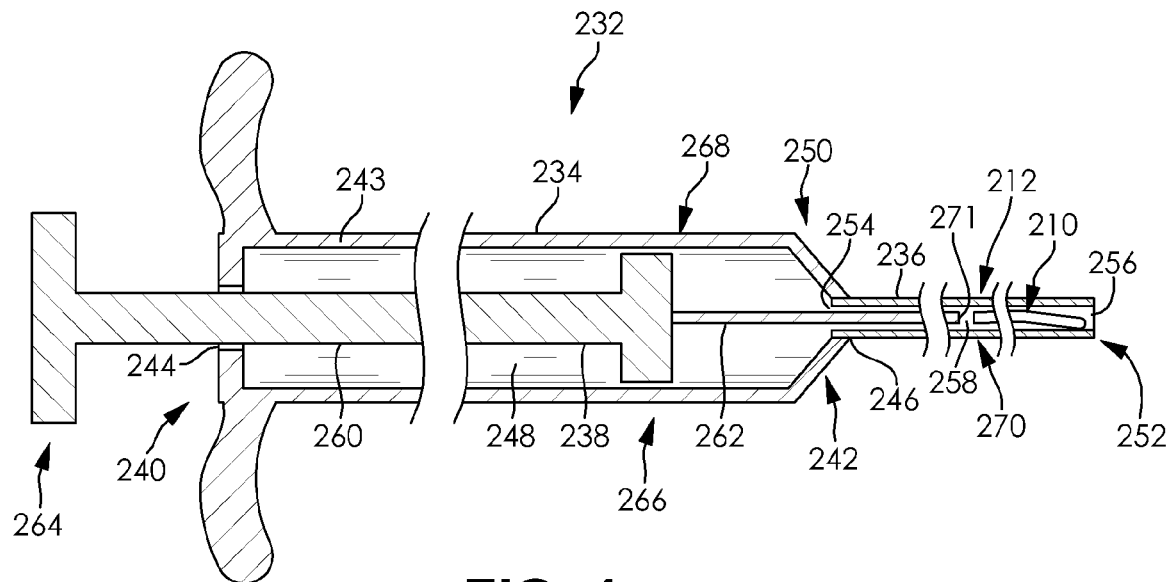
FIG. 4 illustrates a sectional view of an exemplary delivery system and catheter.

FIG. 4 illustrates a first exemplary delivery system 232 and catheter 210. The delivery system 232 comprises a housing 234, cannula 236, and a pusher 238.

The housing 234 has a housing proximal end 240, a housing distal end 242, a wall 243, and defines a first housing opening 244, a second housing opening 246, and a housing lumen 248. The first housing opening 244 is disposed on the housing proximal end 240 and the second housing opening 246 is disposed on the housing distal end 242. The housing lumen 248 extends between the first housing opening 244 and the second housing opening 246.

Housing 234 can be formed of any suitable material and have any suitable structural arrangement, and skilled artisans will be able to select a suitable material and structural arrangement to form a housing according to a particular embodiment based on various considerations, including the desired bodily passage within which a catheter is to be deployed. Example materials considered suitable include, but are not limited to, polymers, such as nylon, polyethylene, and polycarbonate, a mixture thereof, or any other suitable material.

Cannula 236 has a cannula proximal end 250, a cannula distal end 252, and defines a first cannula opening 254, a second cannula opening 256, and a cannula lumen 258. The first cannula opening 254 is disposed on the cannula proximal end 250 and the second cannula opening 256 is disposed on the cannula distal end 252. The cannula lumen 258 extends between the first cannula opening 254 and the second cannula opening 256. Cannula proximal end 250 is attached to housing distal end 242 such that housing lumen 248 and cannula lumen 258 are in fluid communication.

Cannula 236 is rigid, or substantially rigid, and can be formed of any suitable material, and skilled artisans will be able to select a suitable material to form a cannula according to a particular embodiment based on various considerations, including the desired bodily passage within which a catheter is to be deployed. Example materials considered suitable include, but are not limited to, metals, such as stainless steel, titanium, nickel titanium, nickel titanium alloys (e.g., nitinol), and plastics, such as nylon, polyethylene, and polycarbonate.

Cannula 236 can optionally include any suitable structure disposed along the cannula length to assist with maintaining catheter 210 within cannula lumen 258 and/or to provide a user with a mechanism to achieve fine motor control of the delivery system 232, and skilled artisans will be able to select a suitable structure according to a particular embodiment based on various considerations, such as the bodily passage within which a catheter is intended to be deployed. Example structures considered suitable include, but are not limited to, a collet, a control handle such as any of those described in co-pending U.S. Provisional Patent Application No. 61/533,190 (filed Sep. 10, 2011), and hereby incorporated by reference in its entirety, and any other structure capable of providing a releasable radially inward force on a cannula. For example, a control handle can be disposed on the cannula along the portion of the cannula length that contains a catheter.

The pusher 238 has a first portion 260 and a second portion 262. The first portion 260 has a first proximal end 264 and a first distal end 266 and the second portion 262 has a second proximal end 268 and a second distal end 270. The pusher 238 has a pusher length that extends from the first proximal end 264 to the second distal end 270.

The first portion 260 is slidably disposed within the housing 234 and extends through the first housing opening 244 such that the first proximal end 264 is disposed proximal to the housing proximal end 240 and the first distal end 266 is disposed within housing lumen 248. The second proximal end 268 is attached to the first distal end 266 and the second distal end 270 is slidably disposed in cannula lumen 258. The second portion 262 is attached to the first portion 260 such that when a force is applied to the first portion 260 (e.g., first proximal end 264) axial movement of the first portion 260 is transferred to the second portion 262.

The second distal end 270 defines a distal surface 271 that is adapted to engage the catheter proximal end 212 to deploy the catheter 210 upon the application of a distal force on pusher 238. Thus, the second distal end 270 is adapted to engage the proximal end 212 of catheter 210 such that upon the application of a distal force on pusher 238, axial movement of pusher 238 is transferred to catheter 210. The transfer of axial movement between pusher 238 and catheter 210 allows for catheter 210 to move from a first straight, or substantially straight, configuration when the catheter 210 is housed within cannula lumen 258, to a second configuration, which defines bend and coil when catheter 210 is free, or substantially free, of cannula lumen 258.

Therefore, pusher 238 has a first configuration and a second configuration. In the first configuration, the second distal end 270 of pusher 238 is positioned such that the catheter 210 is disposed within cannula lumen 258. In the second configuration, the second distal end 270 of pusher 238 is positioned such that catheter 210 is free, or can become free, of cannula lumen 258. Thus, in the second configuration, the second distal end 270 of pusher 238 can be positioned at various locations along the length of cannula 236, depending on the catheter length, and skilled artisans will be able to select a suitable position for a second distal end according to a particular embodiment based on various considerations, including the catheter length. Example locations considered suitable for placement of a second distal end of a pusher when the pusher is in a second configuration include, but are not limited to, positioning a second distal end proximal to a cannula distal end, positioning a second distal end at a cannula distal end, and positioning a second distal end distal to a cannula distal end.

While delivery system 232 has been described and illustrated as having catheter 210 disposed in cannula 236, it is considered suitable to include any suitable catheter within cannula 236. Skilled artisans will be able to select a suitable catheter according to a particular embodiment based on various considerations, including the desired treatment intended to be performed. Example catheters considered suitable include, but are not limited to, any catheter described herein (e.g., catheter 10, catheter 110, catheter 210, catheter 310, catheter 810), and any other suitable catheter.

While catheter 210 has been described as being disposed within cannula lumen 258 and substantially straight when pusher 238 is in the first configuration, any suitable length of a catheter can be disposed within a cannula when a pusher is in the first configuration, and skilled artisans will be able to select a suitable length of a catheter to position within a cannula lumen according to a particular embodiment based on various considerations, such as the bodily passage within which the catheter is intended to be deployed. Example lengths of a catheter to position within a cannula lumen when a pusher is in a first configuration include, but are not limited to, at least a portion of a catheter, the entire length of a catheter, the portion of the catheter proximal to a bend, the portion of the catheter distal to a bend, the portion of the catheter proximal to a coil, and the portion of the catheter distal to a coil. The portion of the catheter that is disposed within the cannula lumen has a first configuration and a second configuration. In the first configuration, the portion of the catheter that is disposed within the cannula lumen is straight, or substantially straight. In the second configuration, the catheter is free, or substantially free, of the cannula and defines a bend(s) and coil(s).

Figure 4A:
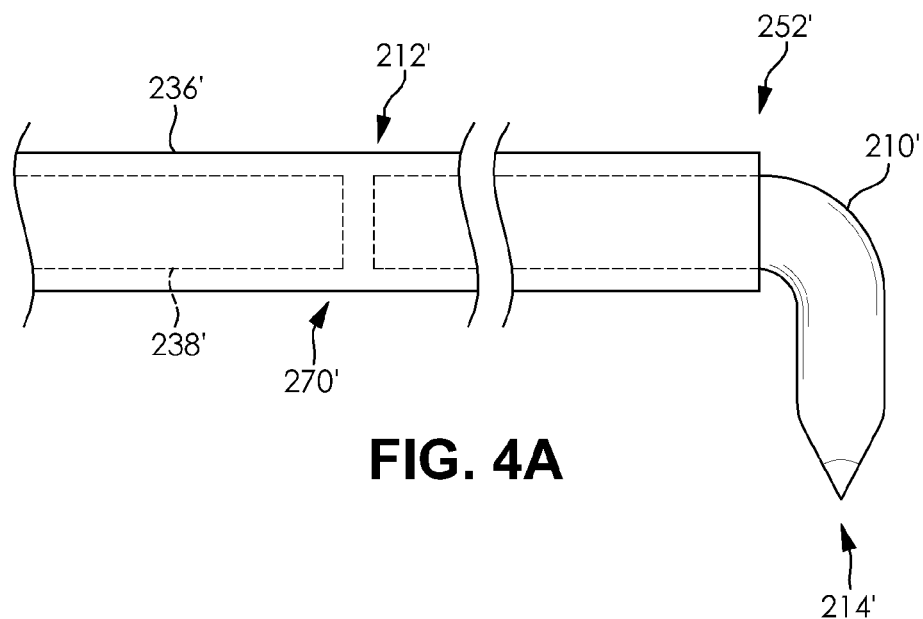
FIG. 4A illustrates a side view of the distal end of another exemplary delivery system and catheter.

For example, as illustrated in FIG. 4A, when pusher 238' is in the first configuration, the second distal end 270' of pusher 238' is positioned such that a portion of catheter 210' is disposed within cannula lumen 258 and a portion of catheter 210' (e.g., catheter distal end 214') is disposed distal to the cannula distal end 252'. In the illustrated embodiment, the portion of catheter 210' that is disposed distal to the cannula distal end 252' forms a bend (e.g., bend is disposed distal to coil) relative to cannula 236'. It is considered advantageous to position a portion of catheter 210' distal to cannula distal end 252' at least because it provides a mechanism for introducing the distal end 214' of the catheter 210' into a bodily passage through an opening prior to applying an axial force to pusher 238'.

The first portion 260 of pusher 238 is rigid, or substantially rigid, and can be formed out of any suitable material, and skilled artisans will be able to select a suitable material for a first portion of a pusher according to a particular embodiment based on various considerations, such as the material forming the second portion of a pusher. Example materials considered suitable to form the first portion of a pusher include, but are not limited to metals, such as stainless steel, titanium, nickel titanium, nickel titanium alloys (e.g., nitinol), and plastics, such as nylon, polyethylene, high-density polyethylene, and polycarbonate.

The second portion 262 of pusher 238 is flexible, or substantially flexible, and can be formed of any suitable material that allows for second portion 262 to travel through cannula lumen 258. Skilled artisans will be able to select a suitable material for a second portion of a pusher according to a particular embodiment based on various considerations, such as the material forming the first portion of a pusher. Example materials considered suitable to form the second portion of a pusher include, but are not limited to metals, such as stainless steel, titanium, nickel titanium, nickel titanium alloys (e.g., nitinol), and plastics, such as nylon, polyethylene, high-density polyethylene, and polycarbonate, or a combination of metal and plastic. When a second portion is formed of a metal, it is considered advantageous to form the second portion of a flexible metal and/or coiled wire such that navigation through the cannula lumen of a delivery system can be accomplished.

Attachment of the second portion 262 of pusher 238 to the first portion 260 of pusher 238 can be accomplished using any suitable method of attachment, and skilled artisans will be able to select a suitable method of attachment according to a particular embodiment based on various considerations, such as the bodily passage within which a catheter is intended to be deployed. An example method of attachment considered suitable between a second portion and a first portion includes, but is not limited to, insert molding.

Alternative to pusher 238 having a first portion 260 and a second portion 262, a delivery system can include a pusher that includes only a first portion. In this alternative delivery system the catheter length is greater than the catheter length of a catheter when the pusher includes a second portion, allowing the catheter to extend into the housing lumen. It is considered advantageous to reduce the diameter of the housing lumen when a pusher only includes a first portion to increase the structural stability of a catheter having a length disposed within the housing lumen.

While the distal end 270 of pusher 238 has been described and illustrated as defining a distal surface 271, any suitable structural arrangement for transferring axial movement between a pusher and a catheter and/or capable of releasably attaching a catheter to a pusher is considered suitable. Skilled artisans will be able to select a suitable structural arrangement based on various considerations, including the desired bodily passage within which a catheter is intended to be disposed.

For example, as illustrated in FIG. 13, alternative to defining a distal surface 271 as shown in FIG. 4, the distal end 1270 of the second portion 1262 of pusher 1238 is adapted to extend distal to the cannula distal end 1252 and defines a collet 1272. Collet 1272 defines recess 1273, has a plurality of notches 1274, and has a first configuration and a second configuration. FIG. 13 illustrates collet 1272 in a first configuration in which collet 1272 is free, or substantially free, of cannula 1236 such that collet 1272 defines a first outer diameter 1275. In the second configuration, not shown, collet 1272 is disposed within, or substantially within, cannula lumen 1258 and defines a second outer diameter that is less than the first outer diameter 1275. Moving the pusher 1238 from the first configuration to the second configuration can be accomplished by applying a proximal force on pusher 1238.

Catheter 1210 can be releasably attached to pusher 1238 by positioning catheter distal end 1212 within the recess 1273 of collet 1272 when collet 1272 is in the first configuration and subsequently moving collet 1272 to the second configuration. Releasing catheter 1210 from collet 1272 can be accomplished by applying a distal force on pusher 1238 to move collet 1272 from its second configuration to its first configuration.

While collet 1272 has been illustrated as having a tapered outer surface and a plurality of notches 1274 (e.g., kerfs), any suitable number of notches or structural arrangement capable of exerting a clamping force on a catheter is considered suitable to include in a delivery system. Skilled artisans will be able to select a suitable number of notches and/or structural arrangement according to a particular embodiment based on various considerations, such as the structural arrangement of a catheter.

Figure 14:
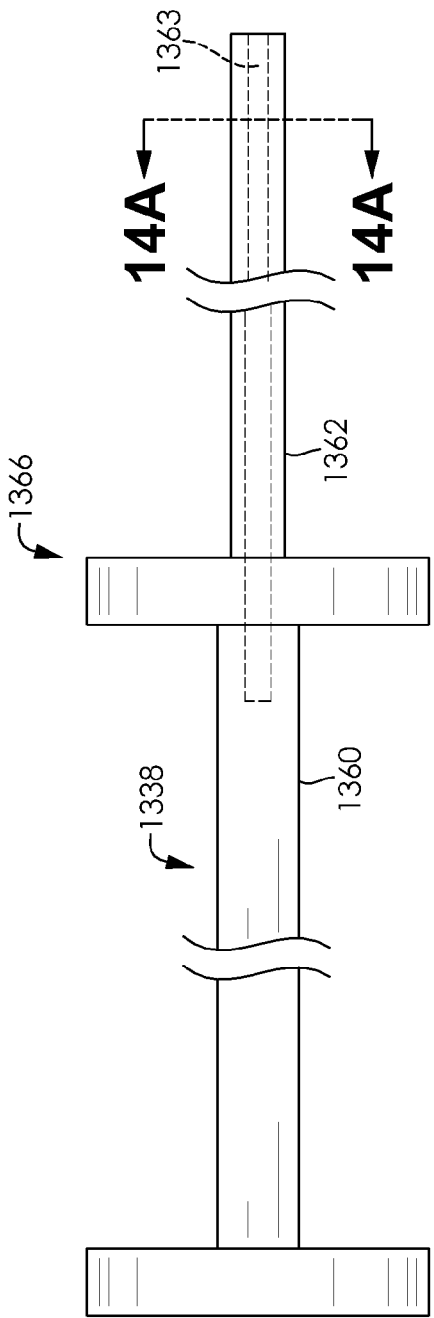
FIG. 14 illustrates a side view of an exemplary pusher free of a delivery system.
Figure 14A:
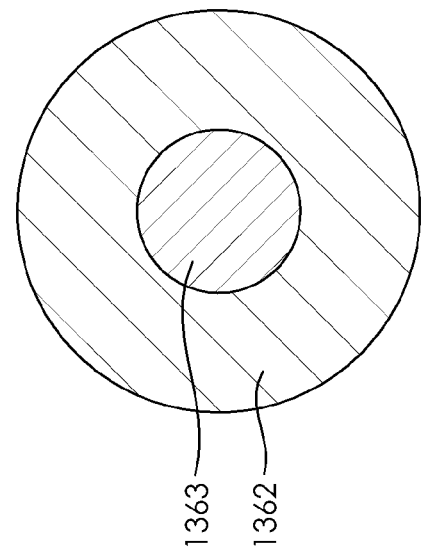
FIG. 14A illustrates a sectional view of the pusher illustrated in FIG. 14, taken along line 14A-14A.

Optionally, any of the herein described pushers can include a reinforcing member, as illustrated in FIGS. 14 and 14A. FIG. 14 illustrates pusher 1338, which is similar to pusher 238, except as described, free of a housing. The pusher 1338 has a first portion 1360, a second portion 1362, and a reinforcing member 1363. In the illustrated embodiment, reinforcing member 1363 extends through the second portion 1362 of pusher 1338 and into the distal end 1366 of the first portion 1360.

The reinforcing member 1363 can be formed of any suitable material and be positioned within the pusher 1338 using any suitable method. Skilled artisans will be able to select a suitable material for a reinforcing member and method of positioning a reinforcing member within a pusher according to a particular embodiment based on various considerations, including the desired bodily passage within which a catheter is intended to be deployed. Example materials considered suitable for a reinforcing member include, but are not limited to, metals, such as stainless steel, titanium, nickel titanium, and nickel titanium alloys (e.g., nitinol). Example methods of positioning a reinforcing member within a pusher include, but are not limited to, creating a passageway through the second portion of a pusher and into the first portion of the pusher and inserting a reinforcing member within the passageway, and forming the pusher around a reinforcing member (e.g., insert molding, gluing).

While FIG. 14 has been illustrated and described as including a reinforcing member 1363 through the length of the second portion 1362 of pusher 1338 and into the distal end 1366 of the first portion 1360 of pusher 1338, any suitable length of a reinforcing member can be included in a pusher. Skilled artisans will be able to select a suitable length of a reinforcing member and a suitable location to position a reinforcing member according to a particular embodiment based on various considerations, including the desired bodily passage within which a catheter is intended to be deployed. Example lengths of a reinforcing member considered suitable include, but are not limited to, a reinforcing member that extends from the distal end of a pusher, or a location proximal to the distal end of a pusher, to the proximal end of the pusher, to the proximal end of the second portion of the pusher, to a location between the proximal end of the second portion of the pusher and the proximal end of the first portion of the pusher, and to a location between the proximal end of the second portion of the pusher and the distal end of the second portion of the pusher.

Figure 5:
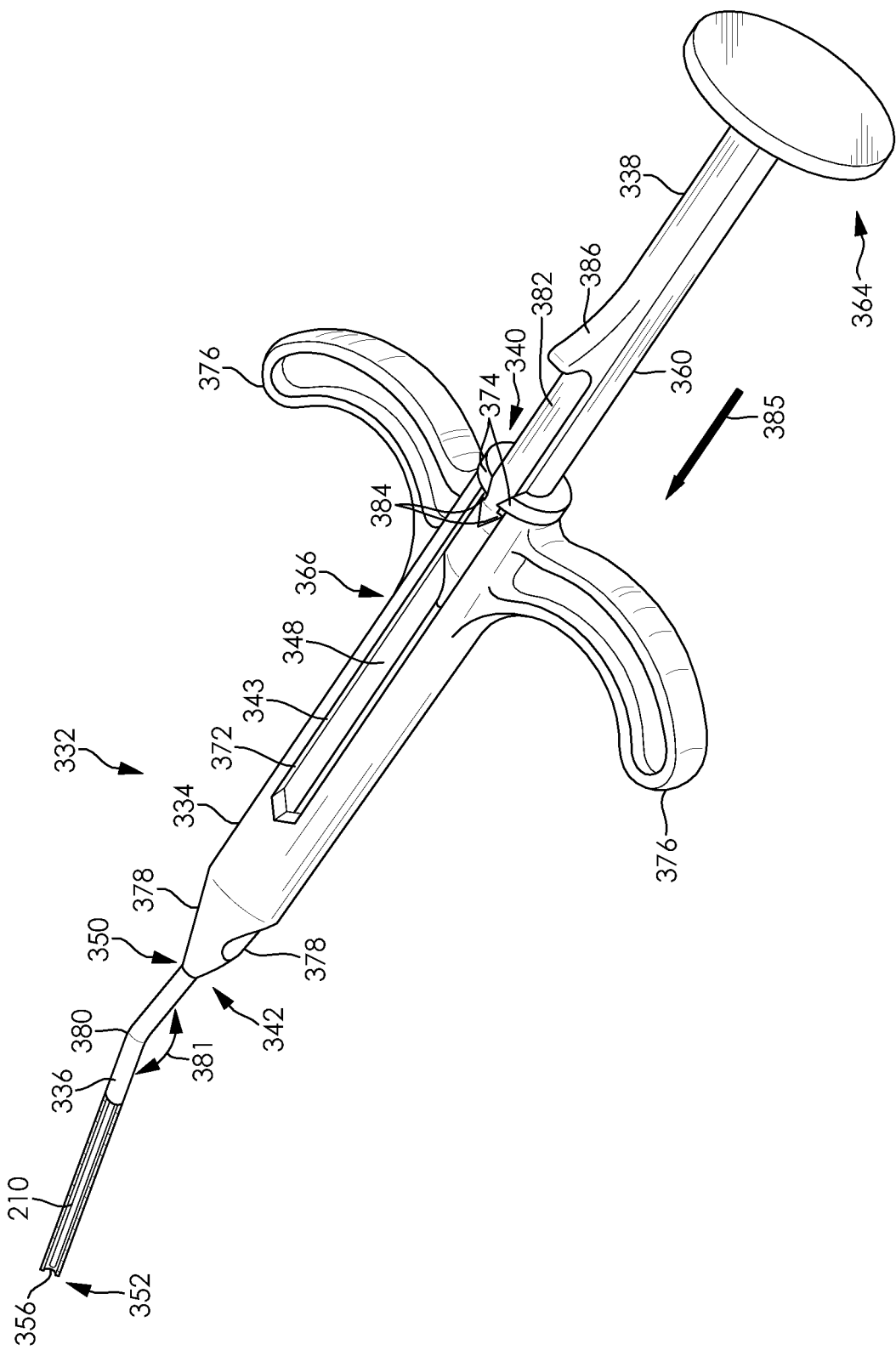
FIG. 5 illustrates a partial sectional view of another exemplary delivery system and catheter.

FIG. 5 illustrates a second exemplary delivery system 332 and catheter 210. The delivery system 332 is similar to delivery system 232 illustrated in FIG. 4, and described above, except as detailed below. With respect to delivery system 332, reference numbers in FIG. 5 refer to the same structural element or feature referenced by the same number in FIG. 4, offset by 100. Thus, the delivery system 332 has a housing 334, cannula 336, and a pusher 338.

In the illustrated embodiment, housing 334 defines a slot 372, protuberances 374, finger flanges 376, and grooves 378. Pusher 338 defines a raised track 382, protuberances 384, and finger flange 386. In addition, cannula 336 defines a bend 380 along the cannula length.

Slot 372 is elongated and extends from the housing proximal end 340 towards the housing distal end 342 and through the wall 343 of the housing 334. Slot 372 provides access to housing lumen 348. Slot 372 can comprise any suitable length and width that allows raised track 382 to be slidably disposed within slot 372, as described below. Skilled artisans will be able to select a suitable structural arrangement for a slot according to a particular embodiment based on various considerations, including the structural arrangement of a pusher intended to be used with the housing.

Each of the protuberances 374 extends into slot 372 and tapers from the distal end of the protuberance to the proximal end of the protuberance. Protuberances 374 can have any suitable length and define any suitable taper such that protuberances 384 can pass through the length of housing 334 that defines protuberances 374 in at least the distal direction. Skilled artisans will be able to select a suitable structural arrangement for the protuberances of a housing according to a particular embodiment based on various considerations, including the structural arrangement of a pusher intended to be used with the housing.

Each of the finger flanges 376 extends radially outward from housing 334 and defines a curve along its length. Finger flanges 376 advantageously provide structure for a user to grasp delivery system 332 and initiate axial movement between housing 334 and pusher 338.

Each of the grooves 378 defines a depression that extends into the wall 343 of housing 334 and provides a mechanism for a user to place the delivery system 332 between one or more fingers such that rotation of the delivery system 332 can be achieved. While particular structural arrangements have been described and illustrated for finger flanges 376 and grooves 378, other structural arrangements are considered suitable. Skilled artisans will be able to select a suitable structural arrangement for a finger flange and a groove according to a particular embodiment based on various considerations, including the structural arrangement of a pusher intended to be used with the housing. Optionally, finger flanges 376 and/or grooves 378 can be omitted from delivery system 332.

In the illustrated embodiment, cannula 336 has a cannula length that extends from the cannula proximal end 350 to the cannula distal end 352 and defines a bend 380 along the cannula length. Bend 380 can be disposed at any suitable angle 381 on cannula 336 and can be formed at any suitable location along the cannula length. Skilled artisans will be able to select a suitable angle and location for a bend according to a particular embodiment based on various considerations, including the bodily passage within which a catheter is to be deployed. The inventors have determined that angles between about 1 degree to about 180 degrees are suitable. In addition, the inventors have determined that angles between about 110 degrees to about 170 degrees are suitable. Furthermore, the inventors have determined that an angle of about, equal to, or substantially equal to 150 degrees is also suitable.

In addition, while a cannula defining a single bend has been illustrated and described, a cannula of a delivery system can define any suitable number of bends along the cannula length, and skilled artisans will be able to select a suitable number of bends for a cannula according to a particular embodiment based on various considerations, such as the bodily passage within which a catheter is intended to be deployed. Example numbers of bends considered suitable for a cannula include, but are not limited to, one, two, three, four and any other number considered suitable for a particular application. For example, a cannula can define a proximal bend and a distal bend along the cannula length and the bends can be defined at angles that are equal to, substantially equal to, or different from one another (e.g., a distal bend that is less than a proximal bend, a distal bend that is greater than a proximal bend).

In the illustrated embodiment, the first portion 360 of pusher 338 defines a raised track 382, protuberances 384, and finger flange 386. Raised track 382 extends radially outward from the first portion 360, along a portion, or the entirety, of the length of pusher 338 and defines a structural arrangement that complements slot 372. Raised track 382, or a portion thereof, is adapted to be slidably disposed within slot 372 such that pusher 338 moves axially along the length of housing 334 when axial force is applied to pusher 338. Raised track 382 can comprise any suitable length and width such that it can be slidably disposed within slot 372. Skilled artisans will be able to select a suitable structural arrangement for a raised track according to a particular embodiment based on various considerations, including the structural arrangement of a housing intended to be used with the pusher.

Protuberances 384 are defined on the distal end of raised track 382 and each protuberance extends radially outward from raised track 382. Each protuberance 384 tapers from the proximal end of the protuberance 384 to the distal end of the protuberance 384. Protuberances 384 can have any suitable length and define any suitable taper such that protuberances 384 can pass through the length of housing 334 that defines protuberances 374 in at least the distal direction. Skilled artisans will be able to select a suitable structural arrangement for the protuberances of a pusher according to a particular embodiment based on various considerations, including the structural arrangement of a housing intended to be used with the pusher.

Raised track 382 and protuberances 384 have a structural arrangement that complements slot 372 and protuberances 374 such that raised track 382 and protuberances 384 can be slidably disposed within slot 372. Protuberances 384 are adapted to pass protuberances 374 in a distal direction, illustrated by arrow 385, such that once protuberances 384 are positioned distal to protuberances 374, the distal end of protuberances 374 and proximal end of protuberances 384 interact to limit proximal movement of pusher 338. The distal end of slot 372 limits distal movement of pusher 338, illustrated by arrow 385. Thus, slot 372 advantageously provides a track for guiding proximal and distal axial movement of pusher 338 along the length of housing 334. For example, when raised track 382 is inserted into slot 372, the distance between each protuberance 374 across slot 372 increases from a first distance to a second, greater, distance to allow protuberances 384 to pass distally past protuberances 374. Once protuberances 384 have past, and are positioned distal to protuberances 374, the distance between each protuberance 374 across slot 372 returns to the first distance such that interaction (e.g., interference) between the distal end of protuberances 374 and proximal end of protuberances 384 can occur.

Finger flange 386 is disposed along the length of raised track 382 and extends radially outward from raised track 382. Finger flange 386 advantageously provides a mechanism for advancing pusher 338 axially in the proximal or distal direction upon the application of force. It is considered advantageous to provide finger flange 386 along the length of pusher 338, between the first proximal end 364 and the first distal end 366, at least to provide additional structure to move pusher 338 in a proximal and distal direction (e.g., by a user with small hands). While a single finger flange 386 has been described and illustrated as disposed along the length of raised track 382, any suitable number of finger flanges can be positioned at any suitable location along the length of pusher 338, and skilled artisans will be able to select a suitable number of finger flanges and a suitable location to position each finger flange 386 according to a particular embodiment based on various considerations, including the structural arrangement of a pusher intended to be used with the finger flange. Example number of finger flanges considered suitable to include, but are not limited to, one, two, three, four and any other number considered suitable for a particular application.

While delivery system 332 has been described and illustrated as having catheter 210 disposed in cannula 336, it is considered suitable to include any suitable catheter within cannula 336. Skilled artisans will be able to select a suitable catheter according to a particular embodiment based on various considerations, including the desired treatment intended to be performed. Example catheters considered suitable include, but are not limited to, any catheter described herein (e.g., catheter 10, catheter 110, catheter 210, catheter 310, catheter 810), and any other suitable catheter.

FIG. 6 illustrates a third exemplary delivery system 432. The delivery system 432 is similar to delivery system 332 illustrated in FIG. 5, and described above, except as detailed below. With respect to delivery system 432, reference numbers in FIG. 6 refer to the same structural element or feature referenced by the same number in FIG. 5, offset by 100. Thus, the delivery system 432 has a housing 434, cannula 436, and a pusher 438.

In the illustrated embodiment, protuberances 374, raised track 382, and protuberances 384, as illustrated in FIG. 5, have been omitted and housing 434 defines a second slot 473 that extends through the wall 443 of housing 434. Second slot 473 extends from a slot first end 475 disposed between the housing proximal end 440 and the housing distal end 442 to a slot second end 477 disposed distal to the slot first end 475 and between the housing distal end 442 and the slot first end 475. Pusher 438 includes a pin 439 that extends radially outward from the first portion 460 of pusher 438. Pin 439 is adapted to be disposed within second slot 473 and provides a mechanism for limiting proximal and distal movement of pusher 438 between the length disposed between slot first end 475 and the slot second end 477.

Pin 439 can be attached to pusher 438 using any suitable method and at any suitable time during the manufacturing process, and skilled artisans will be able to select a suitable method and time to attach a pin to a pusher according to a particular embodiment based on various considerations, including the structural arrangement of the housing of a delivery system. While delivery system 432 has been described as omitting the inclusion of protuberances 374, raised track 382, and protuberances 384, as illustrated in FIG. 5, these elements can optionally be included in delivery system 432.

FIG. 7 illustrates a fourth exemplary delivery system 532. The delivery system 532 is similar to delivery system 332 illustrated in FIG. 5, and described above, except as detailed below. With respect to delivery system 532, reference numbers in FIG. 7 refer to the same structural element or feature referenced by the same number in FIG. 5, offset by 200. Thus, the delivery system 532 has a housing 534, cannula 536, and a pusher 538.

In the illustrated embodiment, slot 372, protuberances 374, finger flanges 376, raised track 382, and protuberances 384, as illustrated in FIG. 5, have been omitted and housing 534 defines slot 573 that extends through the wall 543 of housing 534. Slot 573 extends from a slot first end 575 disposed between the housing proximal end 540 and the housing distal end 542 to a slot second end 577 disposed distal to the slot first end 575 and between the housing distal end 542 and the slot first end 575. Pusher 538 includes two finger flanges 541 each of which has a first portion that extends radially outward from the first portion 560 of pusher 538 and a second portion disposed outside of slot 573. The first portion of each finger flanges 541 is adapted to be disposed within slot 573 and provides a mechanism for limiting proximal and distal movement of pusher 538 between the length disposed between slot first end 575 and the slot second end 577. The second portion is adapted to slide along the outer surface of housing 534 and provides a mechanism for a user to transfer axial movement to pusher 538.

Finger flanges 541 can be attached to pusher 538 using any suitable method and at any suitable time during the manufacturing process, and skilled artisans will be able to select a suitable method and time to attach a flinger flange to a pusher according to a particular embodiment based on various considerations, including the structural arrangement of the housing of a delivery system. While delivery system 532 has been described as omitting the inclusion of slot 372, protuberances 374, raised track 382, and protuberances 384, as illustrated in FIG. 5, these elements can optionally be included in delivery system 532.

While two finger flanges 541 have been illustrated, any suitable number of finger flanges can be included on a delivery device, and skilled artisans will be able to select a suitable number of finger flanges according to a particular embodiment based on various considerations, including the length of the delivery device. Example number of finger flanges considered suitable to include on delivery device include, but are not limited to, one, at least one, two, a plurality, three, and any other number considered suitable for a particular application.

FIGS. 8A and 8B illustrate a fifth exemplary delivery system 632 and catheter 210. The delivery system 632 is similar to delivery system 332 illustrated in FIG. 5, and described above, except as detailed below. With respect to delivery system 632, reference numbers in FIGS. 8A and 8B refer to the same structural element or feature referenced by the same number in FIG. 5, offset by 300. Thus, the delivery system 632 has a housing 634, cannula 636, and a pusher 638.

In the illustrated embodiment, the pusher 638 further comprises an elongate member 700, spring 702, and cap 704.

The first portion 660 of pusher 638 defines passageway 661 and notches 663. Passageway 661 extends along the length of the first portion 660 from an opening on the first proximal end 664 to an opening on the first distal end 666. Notches 663 extend through the body of the first portion and are in communication with passageway 661. The second portion 662 of pusher 638 defines passageway 665 that extends along the length of the second portion 662 from an opening on the second proximal end 668 to an opening on the second distal end 670.

Elongate member 700 comprises a proximal end 706, a distal end 708, a body 710, and flanges 712 that extend radially outward from body 710. Body 710 is slidably disposed through passageway 661 and within passageway 665. Flanges 712 are slidably disposed in notches 663 defined by first portion 660. It is considered advantageous for elongate member 700 to be formed of a flexible, or substantially flexible, material such that advancement through the lumen of a cannula can be achieved.

While elongate member 700 has been described as formed of particular materials, elongate member can be formed of any suitable material, and skilled artisans will be able to select a suitable material for an elongate member according to a particular member based on various considerations, including the desired bodily passage within which a catheter is intended to be deployed. Example materials considered suitable to form an elongate member include, but are not limited to, polymers, such as nylon, polyethylene, polycarbonate, and mixtures thereof, metals such as stainless steel, nickel titanium, coiled materials, or other suitable materials.

Figure 8C:
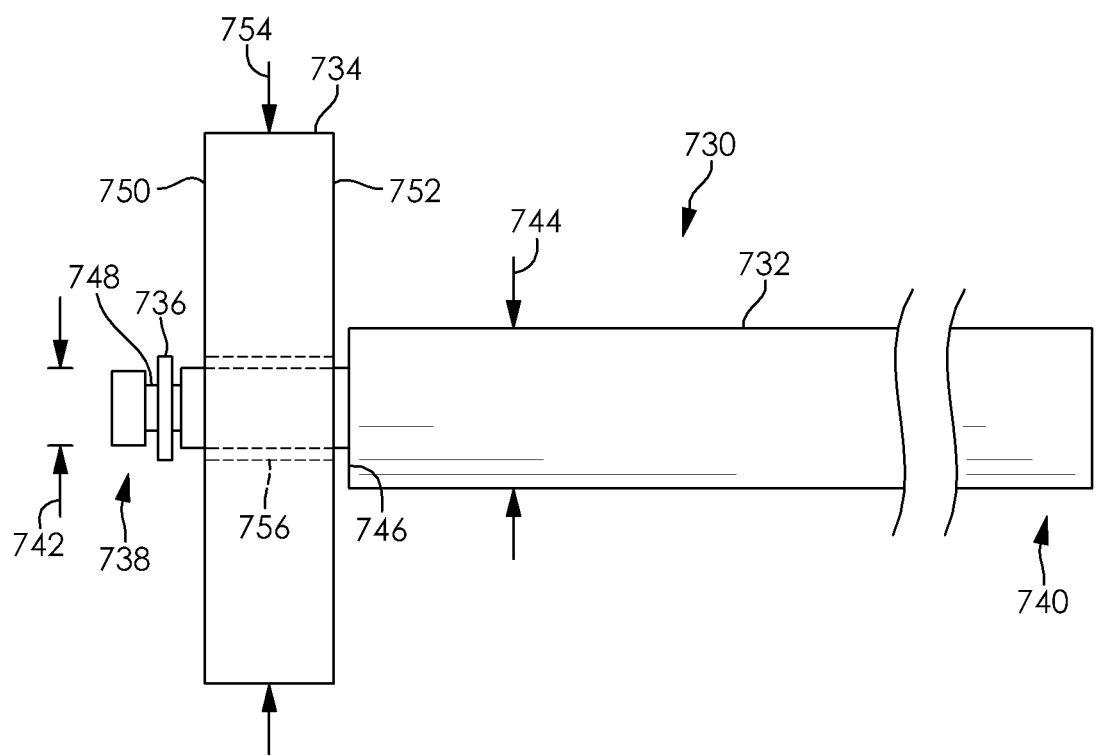
FIG. 8C illustrates an exemplary elongate member free of a delivery system.

In addition, while elongate member 700 has been illustrated as a unitary structure, any suitable number of components can be used to form an elongate member, and skilled artisans will be able to select a suitable number of components according to a particular embodiment based on various considerations. For example, as illustrated in FIG. 8C, an elongate member 730 comprises a body 732, retaining member 734, and a snap pin 736. In the illustrated embodiment, the retaining member 734 replaces flanges 712, as illustrated and described with respect to FIGS. 8A and 8B, and body 732 is rotatable with respect to retaining member 734, as described below.

Body 732 has a proximal end 738, a distal end 740, and defines a first diameter 742, a second diameter 744, shoulder 746, and a recess 748. The first diameter 742 extends from the proximal end 738 and towards the distal end 740 to shoulder 746. The second diameter 744 extends from shoulder 746 to the distal end 740. Recess 748 extends radially into the portion of body 732 that defines the first diameter 742 and is disposed between the proximal end 738 and shoulder 746.

Retaining member 734 has a proximal side 750, a distal side 752, and defines an outside diameter 754 and a passageway 756 that extends from an opening on the proximal side 750 to an opening on the distal side 752.

The first diameter is less than the diameter of passageway 756 and the second diameter is greater than the diameter of passageway 756. The portion of body 732 that defines the first diameter 742 is disposed through passageway 756 of the retaining member 734. The length of the body 732 that defines the first diameter 742 can vary and need only position proximal end 738 and recess 748 proximal to the proximal side 750 of retaining member 734. Snap pin 736 is disposed within recess 748 to rotatably attach body 732 to retaining member 734.

It is considered advantageous to include a body 732 that is free to rotate with respect to retaining member 734 at least because this configuration allows body 732 and a releasably attached catheter (not shown) to freely rotate with respect to the delivery system when in use. The ability of a catheter to rotate with respect to the delivery system is considered advantageous at least because the catheter can adjust to the anatomy of a bodily passage during deployment.

While a snap pin 736 has been illustrated and described as providing an attachment between body 732 and retaining member 734, any suitable component and/or structure capable of maintaining a body within a passageway of a retaining member is considered suitable, and skilled artisans will be able to select a suitable component and/or structure according to a particular embodiment based on various considerations, including the desired bodily passage within which a catheter is intended to be deployed. Example components and/or structures considered suitable include, but are not limited to, O-rings, cotter pins, and retaining rings.

Spring 702 is disposed in passageway 661 proximal to flanges 712 and distal to cap 704. Thus, spring 702 is disposed between flanges 712 and cap 704. In the illustrated embodiment, spring 702 is a compression spring, which exerts a force resisting compression proportional to the distance the spring has been compressed. While spring 702 has been described as a particular type of spring, any suitable spring, formed of any suitable material, and having any suitable compressed and/or uncompressed lengths is considered suitable. Skilled artisans will be able to select a suitable spring, material to form a spring, and suitable compressed and/or uncompressed lengths according to a particular embodiment based on various considerations, including the desired bodily passage within which a catheter is intended to be deployed.

Cap 704 comprises any suitable member capable of retaining spring 702 and elongate member 700 within passageway 661, and skilled artisans will be able to select a suitable member according to a particular embodiment based on various considerations, including the desired bodily passage within which a catheter is intended to be deployed. In the illustrated embodiment, cap 704 comprises a proximal end 720, distal end 722, body 724, and defines recess 726 that extends into body 724 from the distal end 722 towards the proximal end 720. Cap 704 is adapted to releasably attach to the first proximal end 664 of pusher 638. Releasable attachment between cap 704 and first proximal end 664 can be accomplished using any suitable method of attachment, such as an interference fit between the elements.

Delivery system 632 has a first configuration and a second configuration. FIG. 8A illustrates delivery system 632 in the first configuration in which spring 702 exerts a force on the proximal end 706 of elongate member 700 such that flanges 712 interact with the distal end of notches 663. In this configuration, catheter 210 is releasably attached to the distal end 708 of elongate member 700. Releasable attachment between the catheter 210 and elongate member 700 is accomplished by an interference fit between the distal end 708 of elongate member 700 and catheter 210, in which the distal end 708 of elongate member 700 is disposed within catheter lumen 220.

FIG. 8B illustrates delivery system 632 in a second, deployed configuration. In this configuration, a distal force has been placed on pusher 638 such that pusher 638 has advanced distally through housing lumen 648.

As pusher 638 is moved distally from the first configuration to the second configuration, flanges 712 come into contact with housing proximal end 640 such that spring 702 begins to compress. As pusher 638 continues to move distally, the first portion 660 and second portion 662 of pusher 638 advance distally over elongate member 700 such that the second distal end 670 interacts with and transfers axial movement of pusher 638 to the proximal end 212 of catheter 210. The transfer of axial movement from pusher 638 to catheter 210, and the interaction of flanges 712 with housing proximal end 640, causes catheter 210 to become free of elongate member 700 by moving the second portion 662 over the distal end 708 of elongate member 700. Once moved to the second configuration, as shown in FIG. 8B, the catheter 210 is free of elongate member 700 such that catheter 210 can be deployed within a bodily passage, as described in further detail herein.

Optionally, delivery system 632 can include a collar that can be positioned on pusher 638 proximal to flanges 712 and distal to first proximal end 664. Thus, the collar can be positioned between flanges 712 and first proximal end 664. The collar is adapted to releasably attach to pusher 638 using any suitable method (e.g., snap fit) and is considered advantageous at least because when attached to pusher 638 it prevents the elongate member 700 from moving in a proximal direction. Thus, including a collar provides a mechanism for attaching a catheter to the distal end 708 of the elongate member 700.

While particular delivery systems have been described and illustrated herein, any suitable delivery system, having any suitable structural arrangement, is considered suitable to deliver a catheter. Skilled artisans will be able to select a suitable delivery system according to a particular embodiment based on various considerations, including the desired bodily passage within which a catheter is intended to be used.

In addition, any of the elements, features, and/or structural arrangements described herein with respect to any delivery system can be combined in any suitable manner, and skilled artisans will be able to select a suitable element, feature, and/or structural arrangement for a delivery system according to a particular embodiment based on various considerations, such as the desired bodily passage within which a catheter is intended to be deployed.

FIGS. 9A, 9B, 9C, and 9D illustrate the deployment of a catheter 810 within the maxillary sinus cavity 894 using delivery system 332. Catheter 810 is similar to catheter 10 illustrated in FIG. 1, and described above, except as detailed below. Reference numbers in FIGS. 9A, 9B, 9C, and 9D refer to the same structural element or feature reference by the same number in FIG. 1, offset by 800. Thus, catheter 810 has a catheter proximal end 812, a catheter distal end 814, and defines a catheter lumen 820, a bend 822, and a coil 824.

In the illustrated embodiment, the catheter distal end 814 is tapered and catheter 810 defines a plurality of apertures 828 and has a marker 830 disposed at bend 822. Catheter 810 defines bend 822 at an angle equal to, or substantially equal to, 90 degrees and the plurality of apertures 828 is disposed along the length of coil 824, distal to bend 822.

While deployment of the catheter 810 is being described and illustrated as accomplished with delivery system 332, deployment of catheter 810 can be accomplished using any suitable delivery system and any suitable method, such as those described herein. Skilled artisans will be able to select a suitable delivery system and method to deploy a catheter according to a particular embodiment based on various considerations, including the bodily passage within which the catheter is intended to be used. Example methods of delivering a catheter considered suitable include, but are not limited to, using one of the delivery systems described herein, and delivering a catheter over a previously placed guide wire.

In addition, while deployment of catheter 810 is being described and illustrated with respect to the maxillary sinus cavity 894, deployment of a catheter can be accomplished in any suitable bodily passage, sinus passage, or sinus cavity. Skilled artisans will be able to select a suitable location to deploy a catheter according to a particular embodiment based on various considerations, including the desired treatment that is intended to be performed.

Furthermore, while delivery system 332 has been described and illustrated as deploying catheter 810, it is considered suitable to deploy any suitable catheter within a bodily passage, such as maxillary sinus 894. Skilled artisans will be able to select a suitable catheter to deploy in a bodily passage according to a particular embodiment based on various considerations, including the desired treatment intended to be performed. Example catheters considered suitable include, but are not limited to, any catheter described herein (e.g., catheter 10, catheter 110, catheter 210, catheter 310, catheter 810), and any other suitable catheter.

Figure 9A:
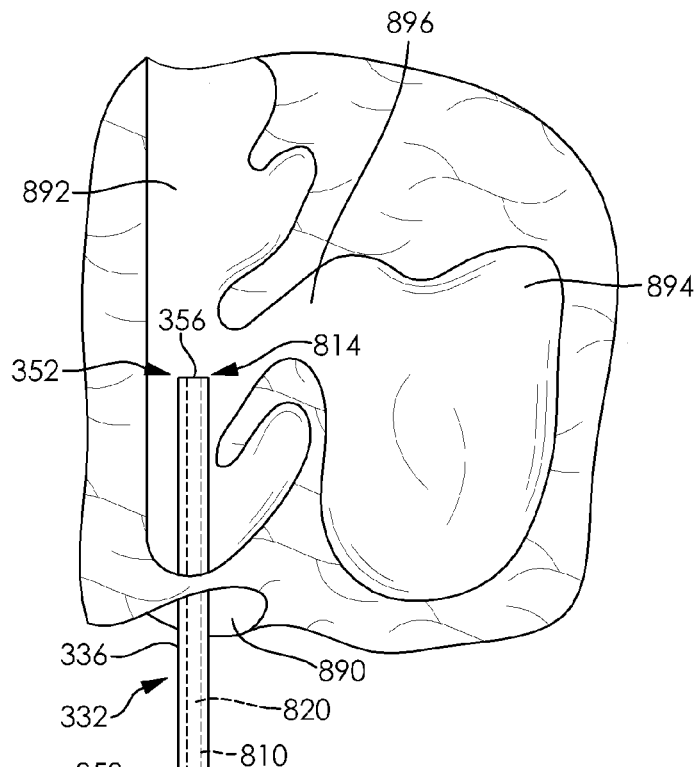
FIG. 9A illustrates a partial sectional view of a patient with a delivery system disposed in a nasal passage.

FIG. 9A illustrates a cannula distal end 352 of delivery system 332 that has been passed through nostril 890 and disposed within nasal passage 892. Catheter 810 is disposed within the cannula lumen 358 in a first, straight, or substantially straight, configuration and catheter distal end 814 is disposed within cannula lumen 358.

Figure 9B:
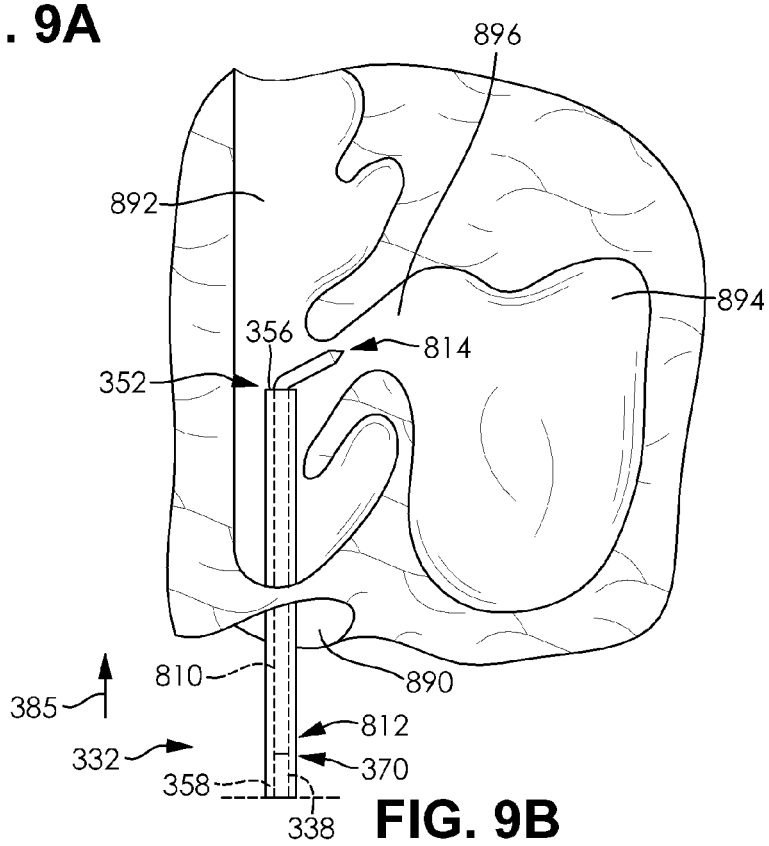
FIG. 9B illustrates a partial sectional view of a patient with a delivery system disposed in a nasal passage in a partially deployed configuration.

In FIG. 9B the second distal end 370 of pusher 338 has been advanced axially in the distal direction, illustrated by arrow 385, and catheter 810 is in a partially deployed configuration, such that catheter distal end 814 is free of cannula lumen 358. As can be seen in FIG. 9B, once the catheter distal end 814 is free of the cannula lumen 358, the catheter 810 begins to move to its second configuration and curves relative to cannula 336 to begin defining coil 824. This is considered advantageous at least because as the catheter 810 moves to the second configuration, the catheter distal end 814 can be navigated into a desired bodily passage, in this case the maxillary sinus cavity 894 through the maxillary sinus ostium 896.

While passing catheter 810 through the maxillary sinus ostium 896 has been described and illustrated, a catheter can be passed through any suitable opening and into any suitable bodily passage, and skilled artisans will be able to select a suitable opening and bodily passage according to a particular embodiment based on various considerations, include the treatment intended to be performed. Example openings considered suitable to pass a catheter through including, but are not limited to, an auxiliary ostium, natural ostium, sinus passage, and the opening of a ventilation tube, such as any of those described in co-pending U.S. patent application Ser. No. 13/158,063 (filed Jun. 10, 2011), and hereby incorporated by reference in its entirety.

Figure 9C:
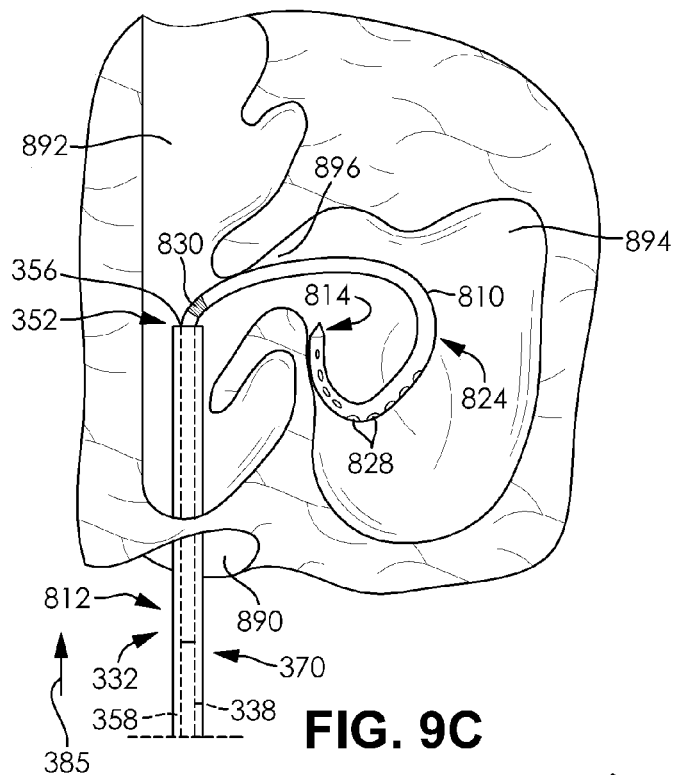
FIG. 9C illustrates a partial sectional view of a patient with a delivery system disposed in a nasal passage in a deployed configuration.

In FIG. 9C pusher 338 has been advanced axially in the distal direction, illustrated by arrow 385, such that catheter 810 has been advanced through the cannula second opening 356 to expose marker 830. The catheter distal end 814 has advanced into the maxillary sinus cavity 894 and catheter 810 has defined coil 824. It is considered advantageous to define coil 824 along a portion of the catheter length at least because it provides a mechanism for holding catheter 810 in place within the maxillary sinus cavity 894 and because it allows catheter 810 to be removed from the maxillary sinus cavity 894 without the application of a great amount of force. In addition, coil 824 is considered advantageous at least because it provides additional structure within the maxillary sinus cavity 894 to introduce a medication or fluid (e.g., through the plurality of apertures 828).

Figure 9D:
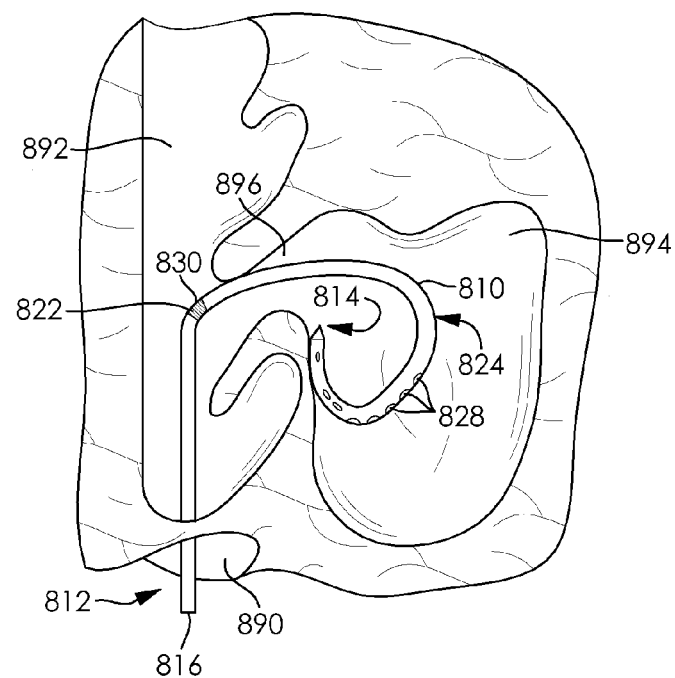
FIG. 9D illustrates a partial sectional view of a patient with a portion of a catheter disposed in a sinus cavity.

FIG. 9D illustrates catheter 810 in a fully deployed second configuration in which catheter 810 defines bend 822 and coil 824. Coil 824 is positioned within the maxillary sinus 894 and the portion of the catheter 810 proximal to bend 822 extends through the nasal passage 892 and out of nostril 890. It is considered advantageous to include bend 822 at least to position the portion of the catheter 810 proximal to the bend 822 down the nasal passage 892, to minimize discomfort, and to allow the catheter proximal end 812 to be positioned such that a user can introduce a medication or fluid into the catheter lumen 820 through the catheter first opening 816 and into the maxillary sinus cavity 894.

Any excess length of catheter 810 extending out of nostril 890 can be trimmed to any suitable length, and skilled artisans will be able to select a suitable length to trim the proximal end of a catheter according to a particular embodiment based on various considerations, including the length of the nasal passage. Example lengths considered suitable include, but are not limited to, trimming the proximal end of a catheter such that the proximal end is disposed within the nasal passage (e.g., distal to the nostril), trimming the proximal end of a catheter such that the proximal end is disposed at the opening of the nasal passage (e.g., nostril), and trimming the proximal end of a catheter such that the proximal end is disposed proximal to the opening of the nasal passage (e.g., nostril).

Figure 10:
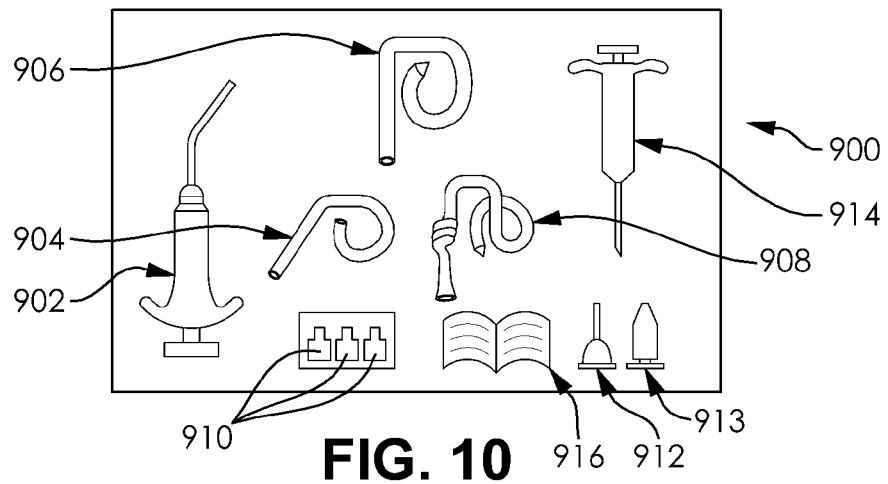
FIG. 10 illustrates an exemplary kit.

FIG. 10 illustrates an exemplary kit 900 comprising a delivery system 902 according to an embodiment, such as delivery system 332 illustrated in FIG. 5; a plurality of catheters 904, 906, and 908 according to an embodiment, such as catheter 10, catheter 110, catheter 210, catheter 310, catheter 810, as illustrated and described herein; a plurality of vials of medication or fluid 910; a first applicator tip 912, a second applicator tip 913; a tool 914 for introducing medication or fluid into a catheter; and instructions for use 916.

While a single delivery system 902, a plurality of catheters 904, 906, and 908, and a plurality of vials of medication or fluid 910 have been described and illustrated in kit 900, any suitable number of delivery systems, catheters, and vials of medication or fluid can be included in kit 900. Skilled artisans will be able to select a suitable number of delivery systems, catheters, and vials of medication or fluid according to a particular embodiment based on various considerations, including the bodily passage within which a catheter is intended to be deployed. Example numbers of delivery systems, catheters, and/or vials of medication or fluid considered suitable to include in a kit include, but are not limited to, one, two, three, four and any other number considered suitable for a particular application.

Furthermore, while delivery system 902 and catheters 904, 906, and 908 have been described and illustrated in kit 900, any suitable delivery system and any suitable catheter can be included in kit 900. Skilled artisans will be able to select a suitable delivery system and catheter according to a particular embodiment based on various considerations, including the bodily passage within which a catheter is intended to be deployed. Example delivery systems considered suitable to include in kit 900 include, but are not limited to, delivery system 232, delivery system 332, delivery system 432, delivery system 532, delivery system 632, a wire guide, and/or any other delivery system considered suitable for a particular application. Example catheters considered suitable to include in kit 900 include, but are not limited to, catheter 10, catheter 110, catheter 210, catheter 310, catheter 810, and/or any other catheter considered suitable for a particular application.

The first applicator tip 912 and second applicator tip 913 are adapted to be releasably attached to a catheter proximal end such that the applicator tip is in communication with the catheter first opening (e.g., catheter first opening 16) of a provided catheter. Each of the first applicator tip 912 and second applicator tip 913 allows for a user to add additional structure (syringe) to the catheter proximal end to pass medication or fluid through the catheter lumen. Each of the first applicator tip 912 and second applicator tip 913 can have any suitable structural arrangement and be formed of any suitable material, and skilled artisans will be able to select a suitable structural arrangement and material for an applicator tip according to a particular embodiment based on various considerations, such as the desired bodily passage within which a catheter is intended to be deployed. For example, an applicator tip can be formed out of a flexible material and be tapered such that a seal is provided when the applicator tip is positioned on the proximal end of a catheter (e.g., within lumen of catheter). Alternatively, an applicator tip may have an outside diameter that is less than the inside diameter of a catheter lumen such that applicator tip can be inserted into a catheter lumen and a medication or fluid can be passed through the catheter lumen.

Any suitable tool 914 for introducing medication or fluid into a catheter can be included in kit 900, and skilled artisans will be able to select a suitable tool according to a particular embodiment based on various considerations, such as the desired bodily passage within which a catheter is intended to be deployed. Example tools considered suitable include, but are not limited to, syringes, and any other suitable device capable of introducing a medication or fluid into the lumen of a catheter.

Figure 11:
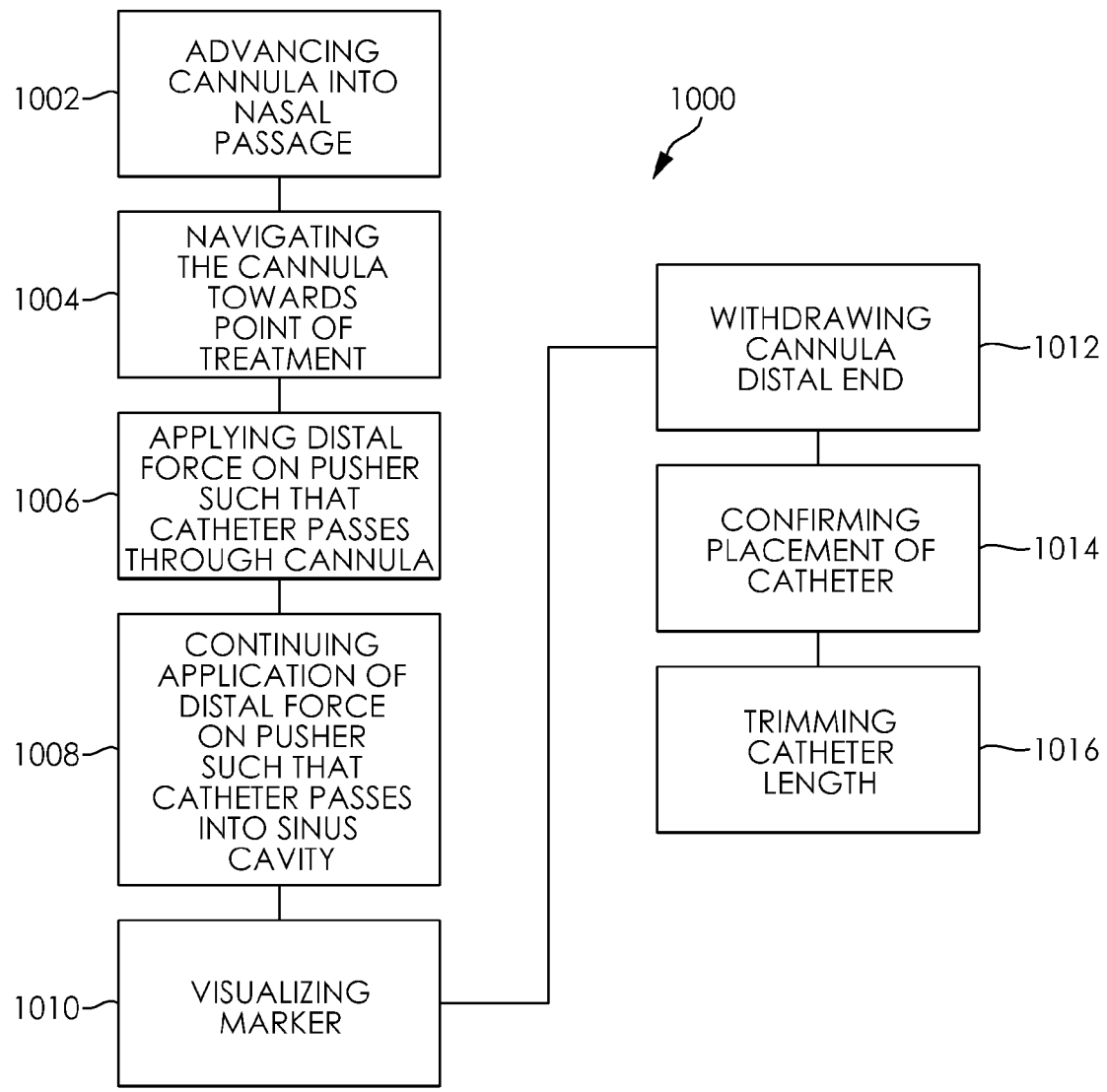
FIG. 11 is a flowchart representation of an exemplary method of deploying a medical device.

FIG. 11 is a flowchart representation of an exemplary method 1000 of deploying a medical device, such as catheter 810 as described herein, into a sinus cavity. An initial step 1002 comprises advancing a delivery system, such as delivery system 332 having a catheter 810 disposed in cannula 336, into a nasal passage such that the cannula distal end 352 is disposed within the nasal passage. Thus, the delivery system has a delivery system proximal end and a delivery system distal end and a portion of the delivery system (e.g., the delivery system distal end) is disposed within the nasal passage. Another step 1004 comprises navigating the cannula distal end 352 towards a point of treatment. Another step 1006 comprises applying a distal force on pusher 338 such that the catheter distal end 814 passes through the cannula second opening 356 and begins to move from a first straight, or substantially straight, configuration to a second configuration that defines coil 824. Another step 1008 comprises continuing the application of a distal force on pusher 338 such that the catheter distal end 814 passes through the sinus passage and into the sinus cavity and catheter 810 defines coil 824 within the sinus cavity. Another step 1010 comprises visualizing marker 830. Another step 1012 comprises withdrawing the delivery device (e.g., cannula distal end 352) from the nasal passage. Another step 1014 comprises confirming placement of catheter 810. Another step 1016 comprises trimming the catheter length.

The step 1002 of advancing a delivery system, such as delivery system 332 having a catheter 810 disposed in cannula 336, into a nasal passage such that the cannula distal end 352 is disposed in the nasal passage can be accomplished using any suitable delivery system or structure capable deploying a catheter into a bodily passage, such as a sinus cavity. While method 1000 has been described as using delivery system 332 to deploy a catheter in a sinus cavity, it is considered suitable to use any suitable delivery system to deploy a catheter. Skilled artisans will be able to select a suitable delivery system according to a particular embodiment based on various considerations, including the desired treatment intended to be performed. Example delivery systems considered suitable include, but are not limited to, delivery system 232, delivery system 332, delivery system 432, delivery system 532, delivery system 632, a wire guide, and any other suitable delivery system.

Furthermore, while method 1000 has been described as deploying catheter 810 into a sinus cavity, it is considered suitable to deploy any suitable catheter into any suitable bodily passage. Skilled artisans will be able to select a suitable catheter and bodily passage to deploy a catheter according to a particular embodiment based on various considerations, including the desired treatment intended to be performed. Example catheters considered suitable include, but are not limited to, catheter 10, catheter 110, catheter 210, catheter 310, catheter 810, and any other suitable catheter.

The step 1004 of navigating the cannula distal end 352 towards a point of treatment can be accomplished by navigating the cannula distal end 352 through the nasal passage and towards a point of treatment (e.g., maxillary sinus ostium, maxillary sinus cavity).

The step 1006 of applying a distal force on pusher 338 such that the catheter distal end 814 passes through the cannula second opening 356 and begins to move from a first straight, or substantially straight, configuration to a second configuration that defines coil 824 can be accomplished by a user applying a distal force on the pusher proximal end 364, or other portion of the pusher 338. The application of a distal force on the pusher proximal end 364, or other portion of the pusher 338, axially advances the pusher 338 in the distal direction such that the pusher distal end 370 engages the catheter proximal end 812 to advance the catheter distal end 814 through cannula second opening 356. When the catheter distal end 814 passes through the cannula second opening 356 it begins to move to its second configuration in which catheter 810 defines coil 824. Thus, the length of catheter 810 that is free of cannula 336 forms a curve, or angle, with respect to cannula 336, which allows for the catheter distal end 814 to be navigated towards, and/or through, a nasal passage, sinus passage, and/or sinus cavity.

An optional step comprises confirming placement of the cannula distal end 352 and/or that the catheter distal end 814 is being passed through a desired sinus passage and/or into a desired sinus cavity. This optional step can be accomplished using any suitable method of visualization, and skilled artisans will be able to select a suitable method to visualize a cannula and/or catheter according to a particular embodiment based on various considerations, such as the desired bodily passage within which a catheter is intended to be deployed. Example methods of visualization include, but are not limited, using direct visualization, fluoroscopy, a scope (e.g., endoscope), transcutaneously, and/or taking an x-ray.

A further example method of visualizing the position of a catheter prior to, during, or subsequent to deployment, includes inserting an optical fiber through the catheter lumen and activating the optical fiber via a light source to determine placement of the catheter transcutaneously (e.g., transilluminating a sinus cavity or other bodily passage). To accomplish passing an optical fiber through a catheter lumen, any of the pushers described herein can define an optical fiber lumen that extends between an opening at, or near, the proximal end of the pusher and an opening at, or near, the distal end of the pusher. The optical fiber can be introduced and passed through the optical fiber lumen of the pusher and also introduced into and/or passed through the catheter lumen.

Any suitable optical fiber defining a light path along its length can be used to accomplish visualization, and a skilled artisan will be able to select a suitable optical fiber according to a particular embodiment based on various considerations, including the desired bodily passage within which a catheter is intended to be deployed. Commercially available optical fibers considered suitable include, but are not limited to, plastic optical fibers and glass optical fibers, with or without cladding. For example, an optical fiber having a proximal end operatively connected, and/or attached, to a light source can be used. The optical fiber can be configured to emit light axially and/or radially and can optionally define one or more curves and/or bends along the optical fiber length.

The step 1008 of continuing the application of a distal force on pusher 338 such that the catheter distal end 814 passes through the sinus passage and into the sinus cavity and catheter 810 defines coil 824 within the sinus cavity can be accomplished by a user continuing to apply a distal force on the pusher proximal end 364, or other portion of the pusher 338, until marker 830 is observed distal to the cannula distal end 352, the pusher has been fully advanced in the distal direction, and/or a suitable length of catheter has been deployed from delivery system 332. It is considered advantageous to include marker 830 on a catheter proximal to coil 824 at least to allow a user to determine when the length of catheter 810 defining coil 824 is free of cannula 336 and has been deployed.

The step 1010 of visualizing marker 830 can be accomplished by direct visualization, x-ray, with a scope, or as otherwise described herein. Step 1010 is considered optional and can be omitted from method 1000.

The step 1012 of withdrawing the cannula distal end 352 from the nasal passage can be accomplished by placing a proximal force on the housing 334, or other portion of the delivery system 332 (e.g., finger flanges 376) to remove the cannula distal end 352 from the nasal passage.

The step 1014 of confirming placement of catheter 810 can be accomplished via any suitable method of visualization, and skilled artisans will be able to select a suitable method to visualize a catheter according to a particular embodiment based on various considerations, such as the desired bodily passage within which a catheter is intended to be deployed. Example methods of visualizing a catheter during, or subsequent to, deployment to confirm its placement include, but are not limited, using direct visualization, fluoroscopy, a scope (e.g., endoscope), transcutaneously, and/or taking an x-ray. Optionally, step 1014 can be omitted from method 1000.

The step 1016 of trimming the catheter length can be accomplished by removing any suitable catheter length from the catheter proximal end using any suitable tool. Skilled artisans will be able to select a suitable catheter length to remove from a catheter and a suitable tool to accomplish such removal according to a particular embodiment based on various considerations, including the bodily passage within which a catheter is intended to be deployed. Example lengths considered suitable to remove from the proximal end of a catheter include, but are not limited to, trimming the proximal end of a catheter such that the proximal end is disposed within the nasal passage (e.g., distal to the nostril), trimming the proximal end of a catheter such that the proximal end is disposed at the opening of the nasal passage (e.g., nostril), and trimming the proximal end of a catheter such that the proximal end is disposed proximal to the opening of the nasal passage (e.g., nostril). Example tools considered suitable to remove a portion of the catheter length include, but are not limited to, scissors, cutting implements, and any other device capable of removing a portion of the catheter length. Step 1016 is considered optional and can be omitted from method 1000.

It is considered advantageous to complete method 1000 in the order illustrated and/or described. It is noted, however, that any order is considered suitable.

While various steps, alternative steps, and optional steps have been described above with respect to deploying a medical device in a sinus passage, these steps, alternative steps, and optional steps can be included in, accomplished concurrently with, and/or accomplished in the alternative to, the method, steps, alternative steps, and/or optional steps described below with respect to method 1100, or any other method described herein.

Alternative to deploying a medical device using a delivery system, a medical device can be deployed over a wire guide, as described herein.

A step comprises advancing a catheter over a wire guide having a wire guide proximal end and a wire guide distal end such that a portion, or the entirety, of the catheter is disposed on the wire guide (e.g., catheter distal end). Thus, the catheter is in a straight, or substantially straight, configuration. Another step comprises advancing the wire guide into a nasal passage such that the wire guide distal end and the catheter distal end are disposed within the nasal passage. Another step comprises navigating the wire guide distal end toward a point of treatment. Another step comprises applying a distal force on the catheter such that it is advanced distally over the wire guide and into an opening, such as those described herein (e.g., sinus passage), and begins to move from a first straight, or substantially straight, configuration to a second configuration that defines a coil. Another step comprises continuing the application of a distal force on the catheter such that the catheter distal end passes through the opening (e.g., sinus passage) and into the sinus cavity and catheter defines the coil within the sinus cavity. Another step comprises withdrawing the wire guide from the nasal passage. Another step comprises confirming placement of catheter. Another step comprises trimming the catheter length.

An optional step that can be completed when a catheter is advanced over a wire guide includes confirming placement of, or visualizing, a marker, or the color of a portion of the catheter. For example, if a marker is disposed at a bend defined by the catheter, then an optional step can comprise confirming that the marker is disposed at, near, or adjacent, to the opening (e.g., sinus passage). Another optional step comprises continuing the application of a distal force on the catheter until the marker is disposed at the opening.

An alternative method of deploying a medical device over a wire guide can be accomplished as described below.

A step comprises advancing a catheter over a wire guide having a wire guide proximal end and a wire guide distal end such that a portion, or the entirety, of the catheter is disposed on the wire guide (e.g., catheter distal end). Thus, the catheter is in a straight, or substantially straight, configuration. Another step comprises advancing the wire guide into a nasal passage such that the wire guide distal end and the catheter distal end are disposed within the nasal passage. Another step comprises navigating the wire guide distal end toward a point of treatment. Another step comprises navigating the wire guide distal end and catheter distal end into an opening, such as those described herein (e.g., sinus passage). Another step comprises withdrawing the wire guide from the nasal passage and maintaining the position of, or applying a distal force on the catheter, such that it is moved from a first straight, or substantially straight, configuration to a second configuration that defines a coil within the sinus cavity. This step can be accomplished by confirming that a marker disposed on the catheter is disposed at the opening. Another step comprises confirming placement of catheter. Another step comprises trimming the catheter length.

If a wire guide is used to deploy a catheter, any suitable wire guide formed of any suitable material and having any suitable structural arrangement can be used. Skilled artisans will be able to select a suitable wire guide and material for a wire guide according to a particular embodiment based on various considerations, including the bodily passage being treated. Example wire guides considered suitable to accomplish one or more steps or methods described herein include, but are not limited to, wire guides having a coiled shaft, wire guides having a mandril shaft with a coiled tip, wire guides having coated coils or mandril, illuminating wire guides, and any other wire guide considered suitable for a particular application. Example materials considered suitable to form a wire guide include but are not limited to, stainless steel, nickel titanium, titanium, platinum, palladium, combinations of materials described herein, and any other material considered suitable for a particular application. It is considered advantageous to use an illuminating wire guide to complete one or more steps or methods described herein to assist with placement of a catheter within a bodily passage. Alternatively, wire guides that have a fiber optic disposed through a lumen defined by the wire guide can be used.

Suitable structural arrangements for a wire guide considered suitable include, but are not limited to, a wire guide that is straight, or substantially straight, along its axial length, a wire guide that defines a bend at an angle about 30 degrees, 60 degree, 90 degrees, or about 180 degrees along its length (e.g., between the wire guide proximal end and wire guide distal end, near the wire guide distal end), and any other structural arrangement considered suitable for a particular application.

FIG. 12 is a flowchart representation of an exemplary method of treatment 1100. Method 1100 is similar to that described above with respect to method 1000, except as described below. An initial step 1102 comprises advancing a delivery system, such as delivery system 332 having a catheter 810 disposed in cannula 336, into a nasal passage such that the cannula distal end 352 is disposed within the nasal passage. Another step 1104 comprises navigating the cannula distal end 352 towards a point of treatment. Another step 1106 comprises applying a distal force on pusher 338 such that the catheter distal end 814 passes through the cannula second opening 356 and begins to move from a first straight, or substantially straight, configuration to a second configuration that defines coil 824. Another step 1108 comprises continuing the application of a distal force on pusher 338 such that the catheter distal end 814 passes through the sinus passage and into the sinus cavity and catheter 810 defines coil 824 within the sinus cavity. Another step 1110 comprises withdrawing the cannula distal end 352 from the nasal passage. Another step 1112 comprises confirming placement of catheter 810. Another step 1114 comprises introducing medication or fluid into catheter lumen 820 and into the sinus cavity. Another step 1116 comprises allowing an interval of time to pass. Another step 1118 comprises introducing medication or fluid into catheter lumen 820 and into the sinus cavity. Another step 1120 comprises allowing for the patient having catheter 810 disposed within the sinus cavity to travel from a first location to a second location. Another step 1122 comprises introducing medication or fluid into catheter lumen 820 and into the sinus cavity. Another step 1124 comprises removing catheter 810 from the sinus cavity and nasal passage.

The step 1112 of confirming placement of catheter 810 can be accomplished via any suitable method of visualization, and skilled artisans will be able to select a suitable method to visualize a catheter according to a particular embodiment based on various considerations, such as the desired bodily passage within which a catheter is intended to be deployed. Example methods of visualizing a catheter during, or subsequent to, deployment to confirm its placement include, but are not limited, using direct visualization, fluoroscopy, a scope (e.g., endoscope), transcutaneously, and/or taking an x-ray. Optionally, step 1014 can be omitted from method 1100.

Each of steps 1114, 1118, and 1122 of introducing medication or fluid into catheter lumen 820 and into the sinus cavity can be accomplished using any suitable device and/or medication. For example, a syringe in communication with the first catheter opening 816 can be used to pass medication or fluid through the catheter lumen 820 and into the sinus cavity through the plurality of openings 828. Alternatively, if a catheter defines a single opening (e.g., second catheter opening 18), the medication or fluid can be introduced into the sinus cavity through such opening. Each of steps 1114, 1118, and 1120 can optionally be completed by any suitable individual (e.g., physician and/or a patient).

Any suitable medication or fluid can be used to accomplished each of steps 1114, 1118, and 1122 and skilled artisans will be able to select a suitable medication or fluid according to a particular embodiment based on various considerations, including the desired treatment intended performed. Example medications and/or fluids considered suitable include, but are not limited to, saline, steroids, antibiotics, anti-inflammatory agents, anti-fungals, surfactants, and antihistamines.

The step 1116 of allowing an interval of time to pass can be accomplished by completing step 1114 and waiting for an interval of time to pass before completing step 1118, 1120 and/or step 1122. Any suitable interval of time is considered suitable, and skilled artisans will be able to select a suitable interval of time according to a particular embodiment based on various considerations, including the condition being treated, and the desired medication or fluid to be used. Example intervals of time considered suitable include, but are not limited to, allowing one or more seconds, one or more minutes, one or more hours, one or more days, one or more weeks, and/or one or more months to pass.

The step 1120 of allowing for the patient having catheter 810 disposed within the sinus cavity to travel from a first location to a second location can be accomplished by the patient traveling from a first location (e.g., physician's office) to a second location (e.g., patient's home). Any suitable location is considered suitable for a first location and a second location, and skilled artisans will be able to select a suitable location according to a particular embodiment based on various considerations, including the condition being treated, and the desired medication or fluid to be used. Step 1120 is considered optional and can be omitted from method 1100.

Each of steps 1114, 1116, 1118, 1120, 1122 can be accomplished one or more times such that a medication or fluid can be introduced into a sinus cavity at one or more times, and/or at one or more locations.

The step 1124 of removing catheter 810 from the sinus cavity and nasal passage can be accomplished by placing a proximal force on the catheter proximal end 812, or other portion of catheter 810, such that the length of catheter 810 disposed within the sinus cavity passes proximally through the sinus passage, through the nasal passage, and out of the nostril.

An optional step comprises trimming the proximal end of the catheter and can be accomplished by removing any suitable catheter length from the catheter proximal end using any suitable tool. Skilled artisans will be able to select a suitable catheter length to remove from a catheter and a suitable tool to accomplish such removal according to a particular embodiment based on various considerations, including the bodily passage within which a catheter is intended to be deployed. Example lengths considered suitable to remove from the proximal end of a catheter include, but are not limited to, trimming the proximal end of a catheter such that the proximal end is disposed within the nasal passage (e.g., distal to the nostril), trimming the proximal end of a catheter such that the proximal end is disposed at the opening of the nasal passage (e.g., nostril), and trimming the proximal end of a catheter such that the proximal end is disposed proximal to the opening of the nasal passage (e.g., nostril). Example tools considered suitable to remove a portion of the catheter length include, but are not limited to, scissors, cutting implements, and any other device capable of removing a portion of the catheter length. This step can be completed prior, or subsequent, to any suitable step within method 1100, and skilled artisans will be able to select a suitable time to complete this optional step according to a particular embodiment based on various considerations, including the desired bodily passage within which a catheter is intended to be deployed. For example, the optional step of trimming a catheter can be accomplished prior, or subsequent, to step 1112 of confirming placement of catheter, step 1114 of introducing medication or fluid into catheter lumen, step 1116 of allowing an interval of time to pass, step 1118 of introducing medication or fluid into catheter lumen, step 1120 of allowing for travel from a first location to a second location, and/or step 1122 of introducing medication or fluid into catheter lumen.

While method 1100 has been described as using delivery system 332 to deploy a catheter in a sinus cavity, it is considered suitable to use any suitable delivery system to deploy a catheter. Skilled artisans will be able to select a suitable delivery system according to a particular embodiment based on various considerations, including the desired treatment intended to be performed. Example delivery systems considered suitable include, but are not limited to, delivery system 232, delivery system 332, delivery system 432, delivery system 532, delivery system 632, a wire guide, and any other suitable delivery system.

While method 1100 has been described as deploying catheter 810 in a sinus cavity, it is considered suitable to deploy any suitable catheter into any suitable bodily passage. Skilled artisans will be able to select a suitable catheter and suitable bodily passage to deploy a catheter according to a particular embodiment based on various considerations, including the desired treatment intended to be performed. Example catheters considered suitable include, but are not limited to, catheter 10, catheter 110, catheter 210, catheter 310, catheter 810, and any other suitable catheter.

It is considered advantageous to complete method 1100 in the order illustrated and/or described. It is noted, however, that any order is considered suitable.

While various steps, alternative steps, and optional steps have been described above with respect to method of treatment 1100, these steps, alternative steps, and optional steps can be included in, accomplished concurrently with, and/or accomplished in the alternative to, the method, steps, alternative steps, and/or optional steps described above with respect to method 1000, or any other method described herein.

The foregoing detailed description provides exemplary embodiments of the invention and includes the best mode for practicing the invention. The description and illustration of embodiments is intended only to provide examples of the invention, and not to limit the scope of the invention, or its protection, in any manner.

What is claimed is:

1. A medical device for treating a sinus cavity, the medical device comprising:
    a delivery system comprising a housing, a cannula, and a pusher;
        the housing having a housing proximal end, a housing distal end, and defining a first housing opening, a second housing opening, and a housing lumen extending between the first housing opening and the second housing opening;

the cannula having a cannula proximal end, a cannula distal end, and defining a first cannula opening, a second cannula opening, and a cannula lumen extending between the first cannula opening and the second cannula opening, the cannula attached to the housing such that the housing lumen and the cannula lumen are in communication;

the pusher having a pusher proximal end, and a pusher distal end slidably disposed in the cannula lumen; and a catheter having at least a portion disposed in the cannula lumen, the catheter having a catheter proximal end, a catheter distal end, a catheter length extending between the catheter proximal end and the catheter distal end, and defining a first catheter opening, a second catheter opening, a bend, a coil, and a catheter lumen extending between the first catheter opening and the second catheter opening;

wherein the pusher distal end is adapted to engage with the catheter proximal end to transfer axial movement to the catheter; and wherein the catheter is adapted to move between a first configuration in which the portion of the catheter disposed within the cannula lumen is substantially straight when disposed in the cannula lumen and a second configuration in which the catheter defines the bend and the coil along the catheter length when the catheter is free of the cannula lumen.

2. The medical device of claim 1, wherein the catheter has a catheter wall; and wherein the catheter defines a plurality of apertures along the catheter length, each aperture of the plurality of apertures extending through the catheter wall and in communication with the catheter lumen.

3. The medical device of claim 2, wherein the plurality of apertures are disposed distal to the bend.

4. The medical device of claim 2, wherein at least two of the plurality of apertures have different diameters.

5. The medical device of claim 1, wherein the cannula has a cannula length extending between the cannula proximal end and the cannula distal end; and wherein the cannula defines a bend along the cannula length.

6. The medical device of claim 1, wherein in the second configuration the catheter defines the bend at an angle between about 45 degrees and about 135 degrees.

7. The medical device of claim 1, wherein in the second configuration the catheter defines the bend at an angle equal to, or substantially equal to, 90 degrees.

8. The medical device of claim 1, wherein the catheter further comprises a marker disposed at the bend.

9. The medical device of claim 1, wherein the catheter proximal end is flared.

10. The medical device of claim 1, wherein the catheter distal end is tapered.

11. A medical device for treating a sinus cavity, the medical device comprising:

a delivery system comprising a housing, a cannula, and a pusher;

the housing having a housing proximal end, a housing distal end, and defining a first housing opening, a second housing opening, and a housing lumen extending between the first housing opening and the second housing opening;

the cannula having a cannula proximal end, a cannula distal end, and defining a first cannula opening, a second cannula opening, and a cannula lumen extending between the first cannula opening and the second cannula opening, the cannula attached to the housing such that the housing lumen and the cannula lumen are in communication;

the pusher having a pusher proximal end, and a pusher distal end slidably disposed in the cannula lumen; and a catheter having at least a portion disposed in the cannula lumen, the catheter having a catheter wall, a catheter proximal end, a catheter distal end, a catheter length extending between the catheter proximal end and the catheter distal end, and defining a first catheter opening disposed on the catheter proximal end, a second catheter opening, a plurality of apertures disposed along the catheter length, a bend, a coil, and a catheter lumen extending between the first catheter opening and the second catheter opening, each aperture of the plurality of apertures extending through the catheter wall and in communication with the catheter lumen;

wherein the pusher distal end is adapted to engage with the catheter proximal end to transfer axial movement to the catheter;

wherein the catheter is adapted to move between a first configuration in which the portion of the catheter disposed within the cannula lumen is substantially straight when disposed in the cannula lumen and a second configuration in which the catheter defines the bend and the coil along the catheter length when the catheter is free of the cannula lumen; and wherein the coil and the plurality of apertures are disposed distal to the bend.

12. The medical device of claim 11, wherein at least two of the plurality of apertures have different diameters.

13. The medical device of claim 11, wherein the cannula has a cannula length extending between the cannula proximal end and the cannula distal end; and wherein the cannula defines a bend along the cannula length.

14. The medical device of claim 11, wherein in the second configuration the catheter defines the bend at an angle between about 45 degrees and about 135 degrees.

15. The medical device of claim 11, wherein in the second configuration the catheter defines the bend at an angle equal to, or substantially equal to, 90 degrees.

16. The medical device of claim 11, wherein the catheter further comprises a marker disposed at the bend.

17. The medical device of claim 11, wherein the catheter proximal end is flared.

18. The medical device of claim 11, wherein the catheter distal end is tapered.

19. A method of deploying a medical device into a sinus cavity, the method comprising the steps of:

advancing a delivery system into a nasal passage such that a portion of the delivery system is disposed within the nasal passage, the delivery system comprising:

a housing having a housing proximal end, a housing distal end, and defining a first housing opening, a second housing opening, and a housing lumen extending between the first housing opening and the second housing opening;

a cannula having a cannula proximal end, a cannula distal end, and defining a first cannula opening, a second cannula opening, and a cannula lumen extending between the first cannula opening and the second cannula opening, the cannula attached to the housing such that the housing lumen and the cannula lumen are in communication;

a pusher having a pusher proximal end, and a pusher distal end slidably disposed in the cannula lumen; and a catheter having at least a portion disposed in the cannula lumen, the catheter having a catheter proximal end, a catheter distal end, a catheter length extending between the catheter proximal end and the catheter distal end, and defining a first catheter opening, a second catheter opening, a bend, a coil, and a catheter lumen extending between the first catheter opening and the second catheter opening, the catheter adapted to move between a first configuration in which the portion of the catheter disposed within the cannula lumen is substantially straight when disposed in the cannula lumen and a second configuration in which the catheter defines the bend and the coil along the catheter length when the catheter is free of the cannula lumen;

navigating the cannula toward a point of treatment;

applying a distal force on the pusher such that the catheter is advanced into said sinus cavity and the catheter moves from the first substantially straight configuration to the second configuration;

introducing medication into the catheter lumen and said sinus cavity; and withdrawing the delivery device from the nasal passage.

20. The method of claim 19, further comprising the steps of:

trimming the catheter length;

allowing for an interval of time to pass; and withdrawing the catheter from said sinus cavity.

* * * * *